(12) United States Patent
Shuler et al.

(10) Patent No.: US 12,257,579 B2
(45) Date of Patent: Mar. 25, 2025

(54) RECIRCULATING UNIDIRECTIONAL PERFUSION FLOW DEVICES AND METHODS OF USE THEREOF

(71) Applicant: Cornell University, Ithaca, NY (US)

(72) Inventors: Michael L. Shuler, Ithaca, NY (US); Ying Wang, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 788 days.

(21) Appl. No.: 16/441,633

(22) Filed: Jun. 14, 2019

(65) Prior Publication Data

US 2020/0070165 A1 Mar. 5, 2020

Related U.S. Application Data

(60) Provisional application No. 62/684,873, filed on Jun. 14, 2018.

(51) Int. Cl.
 *B01L 3/00* (2006.01)
 *C12M 3/06* (2006.01)
 (Continued)

(52) U.S. Cl.
 CPC ..... *B01L 3/502753* (2013.01); *B01L 3/50273* (2013.01); *C12M 27/16* (2013.01);
 (Continued)

(58) Field of Classification Search
 CPC .................. C12M 23/16; C12M 27/16; G01N 2800/7028; B01L 2300/0861;
 (Continued)

(56) References Cited

U.S. PATENT DOCUMENTS 6,743,399 B1 6/2004 Weigl et al.
2003/0096405 A1 5/2003 Takayama et al.
(Continued)

FOREIGN PATENT DOCUMENTS

CN 100590435 C 2/2010
WO 2018126131 A1 7/2018

OTHER PUBLICATIONS

Esch et al., "Modular, Pumpless Body-on-a-Chip Platform for the Co-Culture of GI Tract Epithelium and 3D Primary Liver tissue," Lab Chip 16:2719-29 (2016).

*Primary Examiner* — Dean Kwak
(74) *Attorney, Agent, or Firm* — Troutman Pepper Locke LLP (Rochester)

(57) ABSTRACT

A device is disclosed that comprises a base having first and second reservoirs, each having an inlet and an outlet, and a channel layer comprising an inlet channel in fluid communication with the inlets of the reservoirs, one or more outlet channels in fluid communication with the outlets of the reservoirs, and a channel network comprising at least one channel extending therebetween. In a forward tilted position, a first fluid circuit is formed from the outlet of the first reservoir, through the one or more outlet channels, through the channel network, through the inlet channel, to the both the inlet and outlet of the second reservoir. In a reverse tilted position a second fluid circuit is formed from the outlet of the second reservoir, through the one or more outlet channels, through the channel network, through the inlet channel, to both the inlet and outlet of the first reservoir. Methods of using the device are also disclosed.

10 Claims, 13 Drawing Sheets

(51) Int. Cl.
*C12N 5/071* (2010.01)
*G01N 33/50* (2006.01)

(52) U.S. Cl.
CPC ....... *C12N 5/0671* (2013.01); *G01N 33/5011* (2013.01); *G01N 33/5017* (2013.01); *B01L 2300/0861* (2013.01); *B01L 2400/0406* (2013.01); *B01L 2400/084* (2013.01); *G01N 2800/7028* (2013.01)

(58) Field of Classification Search
CPC ..... B01L 2400/0406; B01L 2400/0457; B01L 2400/084; B01L 3/50273; B01L 3/502753
See application file for complete search history.

(56) References Cited

U.S. PATENT DOCUMENTS

| | | | |
|---|---|---|---|
| 2005/0244283 A1 | 11/2005 | Yao et al. | |
| 2008/0085219 A1 | 4/2008 | Beebe et al. | |
| 2012/0135452 A1* | 5/2012 | Shuler | C12M 29/00 |
| | | | 435/395 |
| 2013/0224845 A1* | 8/2013 | Tsao | B01L 9/527 |
| | | | 435/287.2 |
| 2017/0151560 A1 | 6/2017 | Zhou et al. | |
| 2018/0273888 A1* | 9/2018 | Esch | C12M 21/08 |

* cited by examiner

FIG. 6A
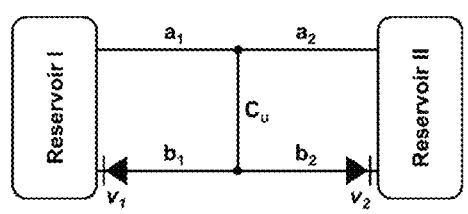
FIG. 6B
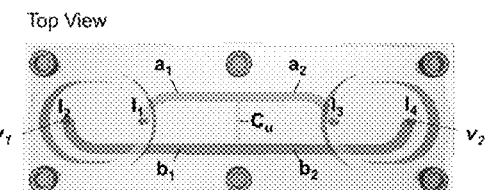
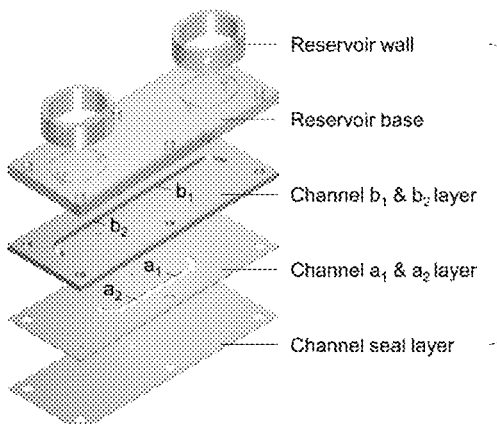
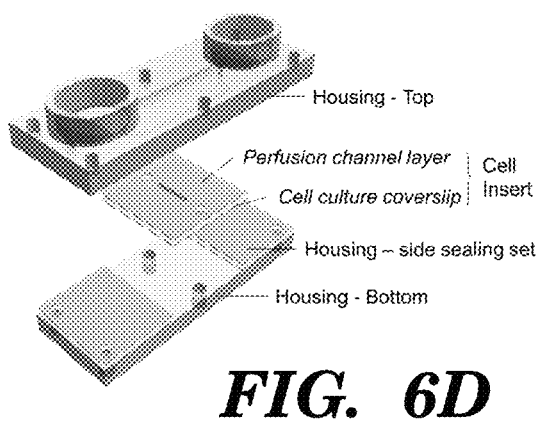
FIG. 6C
FIG. 6D
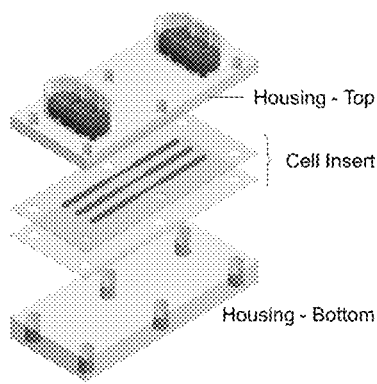
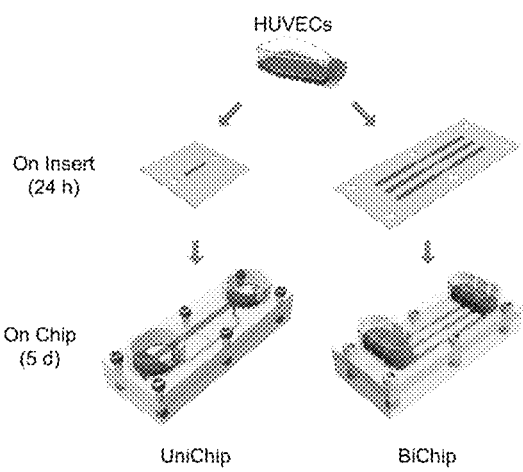
FIG. 6E
FIG. 6F

FIG. 7A
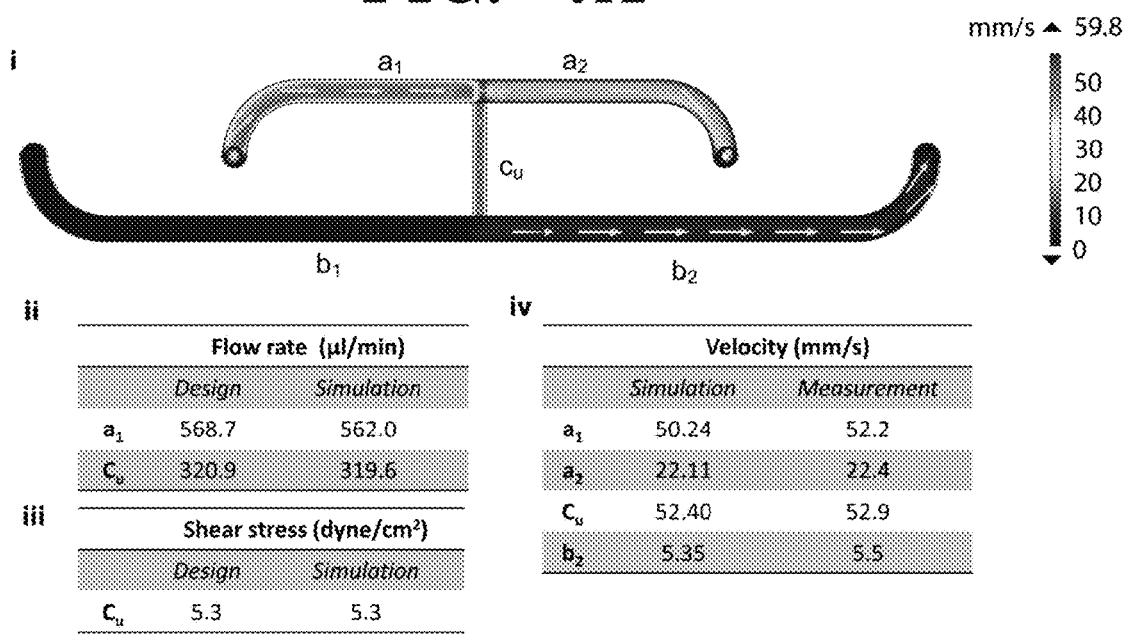
FIG. 7B
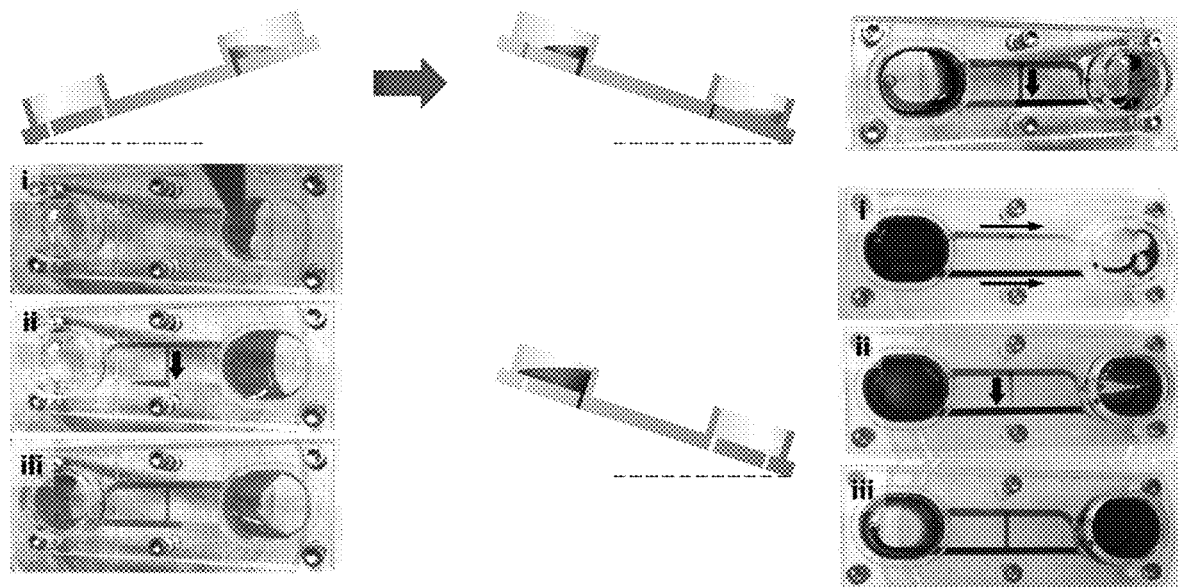
FIG. 7C
FIG. 7D

RECIRCULATING UNIDIRECTIONAL PERFUSION FLOW DEVICES AND METHODS OF USE THEREOF

This application claims the benefit of U.S. Provisional Patent Application Ser. No. 62/684,873, filed Jun. 14, 2018, which is hereby incorporated by reference in its entirety.

GOVERNMENT FUNDING

This invention was made with Government support under Grant Numbers 1R44TR001326-01 and 1U01CA214300-01A1 awarded by the National Institutes for Health. The United States Government has certain rights in the invention.

FIELD

The present application relates to recirculating unidirectional perfusion flow devices and methods of use thereof.

BACKGROUND

There are many applications where a unidirectional flow of fluid over a potential catalyst is desirable. In particular, in vitro microscale biomimetics of the human body, namely, Body-on-a-Chip (BOC) microphysiological systems (MPS), are promising "human surrogates" to be used as in vitro models and tools for the next generation drug screening. These systems integrate various tissue-engineered microscale organ models via microfluidic interconnections that mimic blood circulation.

Various microfluidic platforms have been proposed to enable organ perfusion and interconnection, providing continuous nutrient and oxygen supply, metabolic waste removal, and communication. A pumpless platform that combines gravity-driven flow and a rocking motion to create fluid recirculation within a BOC model was designed, allowing dynamic organ-organ interactions without the need for external pumps and tubing. Such a platform allows design of self-contained and highly integrated systems that are relatively easy and cost-effective to construct and maintain. It has since been used for a variety of organ-on-a-chip models, including "skin", "liver", "gut" and "blood brain barrier", as well as multi-organ microsystems of up to 13 organ models. Recently, the pumpless platform has also proved its great potential in supporting high content analysis in a relatively high throughput format.

The pumpless platform achieves medium recirculation by creating reciprocating flow between a pair of reservoirs. Although such recirculation mode causes little deviation in the pharmacokinetic profiles of drugs compared to closed-loop unidirectional recirculation, it induces oscillatory shear stress, which could potentially affect shear stress (SS)-sensitive tissues, such as the vasculature, kidney and lung. To better accommodate these tissues in a microfluidic MPS, several strategies have been proposed.

In a microfluidic blood-brain barrier (BBB) model, a "step chamber" that offsets the culture plane of the barrier tissue from the channel plane by a distance to minimize the magnitude of bidirectional SS on the cell surface was utilized. This adaptation allowed brain microvascular endothelial cells (BMECs) to survive and maintain their unique BBB phenotype under reciprocating perfusion. In a pumpless gastrointestinal tract (GI)-liver MPS, a backflow channel and a set of passive valves to achieve semi-unidirectional perfusion was used. Fluid circulating between a pair of reservoirs traveled alternately through the organ perfusion channel and the backflow channel. Such system provided unidirectional perfusion for only a fraction of the period and halted flow for the rest of it. In contrast to bidirectional perfusion system, this GI-liver MPS was able to retain the barrier function of the GI tissue for at least 14 days, but was unable to provide a continuous flow.

The present invention is directed to overcoming these and other deficiencies in the art.

SUMMARY

One aspect of the present application relates to a device comprising a reservoir base having a first reservoir and a second reservoir positioned at opposing ends thereof. Each of the first reservoir and the second reservoir have an inlet and an outlet extending through the reservoir base. The device further comprises a channel layer. The channel layer comprises one or more inlet channels in fluid communication with the inlets of the first and second reservoirs, one or more outlet channels in fluid communication with the outlets of the first and second reservoirs, and a channel network comprising at least one channel extending between the one or more inlet channels and the one or more outlet channels. When the device is tilted in a forward tilted position, with respect to a horizontal axis, a first fluid circuit is formed for directing a first flow of fluid from the outlet of the first reservoir, through the one or more outlet channels, through the channel network, through the one or more inlet channels, to the both the inlet and outlet of the second reservoir. When the device is tilted in a reverse tilted position, with respect to the horizontal axis, a second fluid circuit is formed for directing a second flow of fluid from the outlet of the second reservoir, through the one or more outlet channels, through the channel network, through the one or more inlet channels, to the both the inlet and outlet of the first reservoir. The outlets of the first reservoir and the second reservoir are located closer to horizontal axis, about which the device is tilted between the forward tilted position and the reverse tilted position, than the inlets of the first reservoir and the second reservoir, respectively.

Another aspect of the present application relates to a method for delivering a fluid to a catalyst. This method includes providing the device of the present application and providing the catalyst in the at least one channel of the channel network. A fluid is provided in at least one of the first reservoir or the second reservoir. The fluid is delivered to the at least one channel of the channel network through the first and second fluid circuits by alternately tilting the device between the forward tilted position and the reverse tilted position, with respect to the horizontal axis, respectively, to deliver the fluid to the catalyst located therein.

A further aspect of the present application relates to a method for delivering a fluid to a cell culture. This method includes seeding a cell culture in a device including a channel layer comprising an inlet, one or more outlet channels, and a channel network comprising at least one channel extending between the one or more inlet channels and the one or more outlet channels. The channel layer is fluidly coupled to a first reservoir and a second reservoir. Each of the first reservoir and the second reservoir have an inlet and an outlet such that the inlets of the first and second reservoirs are in fluid communication with the one or more inlet channels and the outlets of the first and second reservoirs are in fluid communication with the one or more outlet channels. When the device is tilted in a forward tilted position, with respect to a horizontal axis, a first fluid circuit is formed for directing a first flow of fluid from the outlet of the first reservoir, through the one or more outlet channels, through the channel network, through the one or more inlet channels, to both the inlet and the outlet of the second reservoir. When the device is tilted in a reverse tilted position, with respect to the horizontal axis, a second fluid circuit is formed for directing a second flow of fluid from the outlet of the second reservoir, through the one or more outlet channels, through the channel network, through the one or more inlet channels, to both the inlet and the outlet of the first reservoir. The outlets of the first reservoir and the second reservoir are located closer to the horizontal axis, about which the device is tilted between the forward tilted position and the reverse tilted position, than the inlets of the first reservoir and the second reservoir, respectively. A fluid is provided in at least one of the first reservoir or the second reservoir. The fluid is delivered to the cell culture through the first and second fluid circuits by alternately tilting the device between the forward tilted position and the reverse tilted position, with respect to the horizontal axis, respectively.

Yet another aspect of the present application relates to a method for testing metabolism dependent chemotherapeutic toxicity. This method includes seeding a colon cell culture comprising cancerous cells in a first cell culture chamber of a cell culture insert, a liver cell culture in a second cell culture chamber of the cell culture insert, and a bone marrow cell culture in a third cell culture chamber of the cell culture insert. The cell culture insert is fluidly coupled to a channel layer comprising one or more inlet channels, one or more outlet channels, and a channel network comprising a first channel, a second channel, and a third channel arranged in parallel configuration and extending between the one or more inlet channels and the one or more outlet channels such that the first cell culture chamber is in fluid communication with the first channel, the second cell culture chamber is in fluid communication with the second channel, and the third cell culture chamber is in fluid communication with the third channel. The channel layer is positioned in fluid communication with a reservoir base having a first reservoir and a second reservoir positioned at opposing ends thereof. Each of the first reservoir and the second reservoir have an inlet and an outlet extending through the reservoir base such that the inlets of the first and second reservoirs are in fluid communication with the one or more inlet channels and the outlets of the first and second reservoirs are in fluid communication with the one or more outlet channels. The cell culture insert, channel layer, and the reservoir base are assembled to form a device. When the device is tilted in a forward tilted position, with respect to a horizontal axis, a first fluid circuit is formed for directing a first flow of fluid from the outlet of the first reservoir, through the one or more outlet channels, through the channel network, through the one or more inlet channels, to both the inlet and the outlet of the second reservoir. When the device is tilted in a reverse tilted position, with respect to the horizontal axis, a second fluid circuit is formed for directing a second flow of fluid from the outlet of the second reservoir, through the one or more outlet channels, through the channel network, through the one or more inlet channels, to the inlet of the first reservoir. The outlets of the first reservoir and the second reservoir are located closer to the horizontal axis, about which the device is tilted between the forward tilted position and the reverse tilted position, than the inlets of the first reservoir and the second reservoir, respectively. A fluid is provided in at least one of the first reservoir or the second reservoir. The fluid is delivered to the first, second, and third cell culture chambers through the first and second fluid circuits by alternately tilting the device between the forward tilted position and the reverse tilted position, with respect to the horizontal axis, respectively.

The device of the present application provides a fluid network that allows for long-term, reliable perfusion with continuous, unidirectional flow. The device converts a reciprocating flow input into the continuous, unidirectional perfusion in one or more channels of interest. The device further provides an effective mechanism that prevents backflow in the one or more channels of interest to ensure the unidirectional fluid flow is maintained. The device allows for easy integration of shear stress sensitive materials, such as certain cell tissues onto the device. The device can advantageously be applied to any fluid system that desires unidirectional flow with circulation.

The device of the present application is suitable for long-term culture of shear stress-sensitive tissues. The backflow-proof mechanism of the device ensures reliable unidirectional perfusion even when passive valves fail (e.g. delayed shut-off due to excessive fluid in the reservoirs). The channels (passive valves and the inlet/outlet) connecting to the reservoirs not only contribute to creating the unidirectional perfusion, but also prevent fluid depletion in the perfusion channel(s) in cases where reservoirs are depleted (e.g. excessive evaporation or prolonged holding time at one tilting direction). All these enable a hassle-free operation for long-term perfusion of organ models, especially shear stress-sensitive tissues.

The device of the present application provides a reliable and cost-effective solution for the integration of vasculature and other shear stress-sensitive tissues (e.g. lung and kidney) into pumpless recirculating body-on-a-chip systems. The device can include complicated fluidic networks that have branches for multiple organ perfusion. The device could also include asymmetric designs to achieve pulsatile perfusion if desired. The open reservoirs provide easy access for medium sampling in a recirculating fluid system, as compared to closes-loop fluid systems driven by pneumatic or peristatic pumps. The open reservoirs also allow for the addition of nutrients and/or drugs and/or removal of waste and/or toxic material produced by the cells or breakdown of the nutrients and/or drugs, which is necessary for long term operation. The device can expedite the development and widespread application of high-throughput, high-content microphysiological systems.

BRIEF DESCRIPTION OF DRAWINGS

FIG. 6A-6F illustrate an exemplary system construction and assembly of a demonstration UniChip device of the present application and a control BiChip device. FIG. 6A is a microfluidic circuit diagram of the demonstration UniChip (A). FIG. 6B is a top view of the design. FIG. 6C is an exploded view of a top piece of the housing containing reservoirs and supporting channels constructed from patterned PMMA layers. FIG. 6D is a cell insert composed of a silicon perfusion channel layer and a cell culture coverslip was sandwiched between the top and bottom pieces of the housing for assembly. FIG. 6E is a schematic exploded view of the BiChip, which contains 3 sets of microfluid circuits, each with a pair of reservoirs and a perfusion channel. FIG. 6F illustrates HUVECs seeded onto inserts and cultured for 24 h before assembling the cell inserts onto chips (UniChips or BiChips).

FIGS. 7A-D illustrate computational and experimental analysis of fluid dynamics in a demonstration UniChip. In FIG. 7A, magnitude (color coded) and direction (white arrow) of the velocity field were plotted at half depth plane of each channel (i). The simulated results verified the microfluidic channel design for the flow rate (ii) and shear stress (iii). Flow velocities in different channels measured with dye tracing approach (n=3) were within ±1~4% of the simulation results (iv). The flow direction was visualized with dyes. Red dye placed in one reservoir flows to the other reservoir through the top (inlet) and center channels (FIG. 7B). Once the device is flipped, blue dye is placed in the other reservoir and flows back to the initial reservoir through the inlet and center channels (FIG. 7C). Unidirectional flow is achieved within the center channel (arrows). In cases where excessive fluid (purple dye) completely covers the passive valve and delays the liquid-air interface formation (FIG. 7D), fluid flows from one reservoir to the other through the top and the bottom channels (i, arrows), and starts to flow through the center channel when the interface begins to form. No backwards flow occurs during the whole period.

FIG. 8A), yet no evident morphological change in BiChip perfused cells (FIG. 8D vs. FIG. 8B). Confocal microscopy reveals dense, continuous expression of VE-cadherin along the cell borders in UniChip cultured cells (FIG. 8E), while that in the BiChip group is discontinuous (FIG. 8F). Immunostaining of F-actin with Alexfluor488-phalloidin shows differential F-actin morphology and orientation for the UniChip (FIG. 8G) and BiChip (FIG. 8H) groups. Merged images of VE-cadherin and F-actin staining shows differential F-actin distribution in the two groups (FIGS. 8I,J). Scale bar, 100 μm.

DETAILED DESCRIPTION

The present application relates to fluidic devices. More specifically, the present application relates to recirculating unidirectional perfusion flow devices and methods of use thereof.

One aspect of the application relates to a device comprising a reservoir base having a first reservoir and a second reservoir positioned at opposing ends thereof. Each of the first reservoir and the second reservoir have an inlet and an outlet extending through the reservoir base. The device further comprises a channel layer. The channel layer comprises one or more inlet channels in fluid communication with the inlets of the first and second reservoirs, one or more outlet channels in fluid communication with the outlets of the first and second reservoirs, and a channel network comprising at least one channel extending between the one or more inlet channels and the one or more outlet channels. When the device is tilted in a forward tilted position, with respect to a horizontal axis, a first fluid circuit is formed for directing a first flow of fluid from the outlet of the first reservoir, through the one or more outlet channels, through the channel network, through the one or more inlet channels, to the both the inlet and outlet of the second reservoir. When the device is tilted in a reverse tilted position, with respect to the horizontal axis, a second fluid circuit is formed for directing a second flow of fluid from the outlet of the second reservoir, through the one or more outlet channels, through the channel network, through the one or more inlet channels, to the both the inlet and outlet of the first reservoir. The outlets of the first reservoir and the second reservoir are located closer to horizontal axis, about which the device is tilted between the forward tilted position and the reverse tilted position, than the inlets of the first reservoir and the second reservoir, respectively.

Figure 1A:
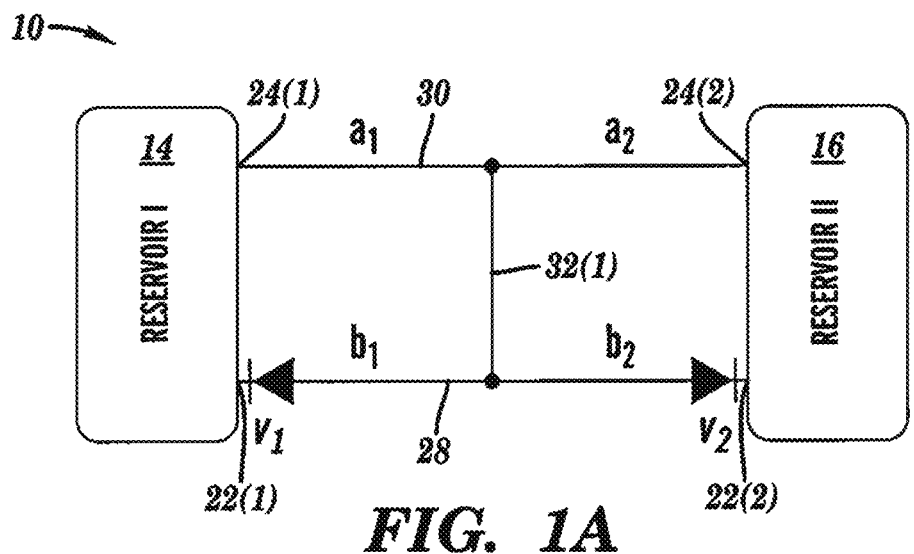
FIG. 1A is a schematic view of a recirculating unidirectional perfusion flow device of the present application.
Figure 1B:
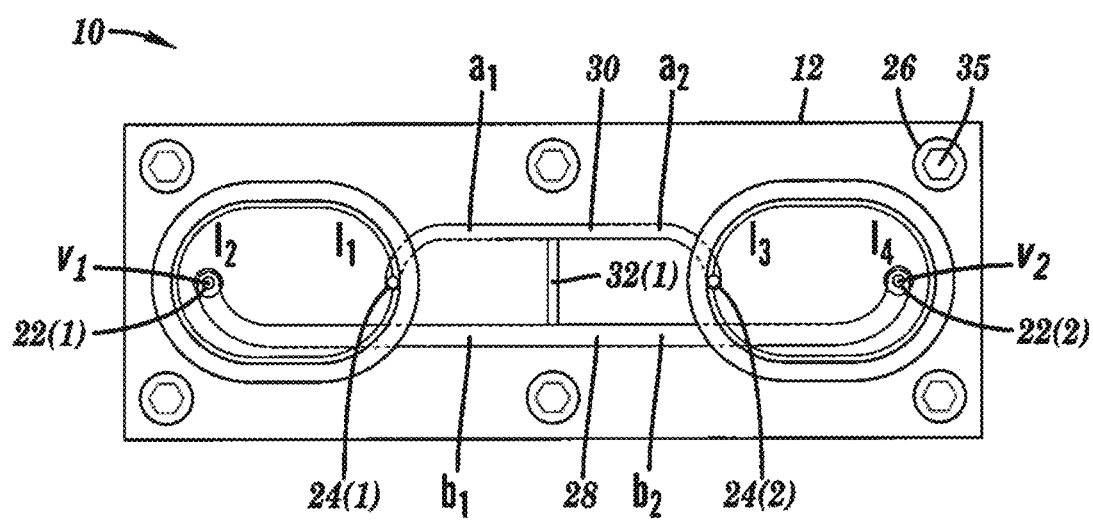
FIG. 1B is a top view of the device of the present application.
Figure 1C:
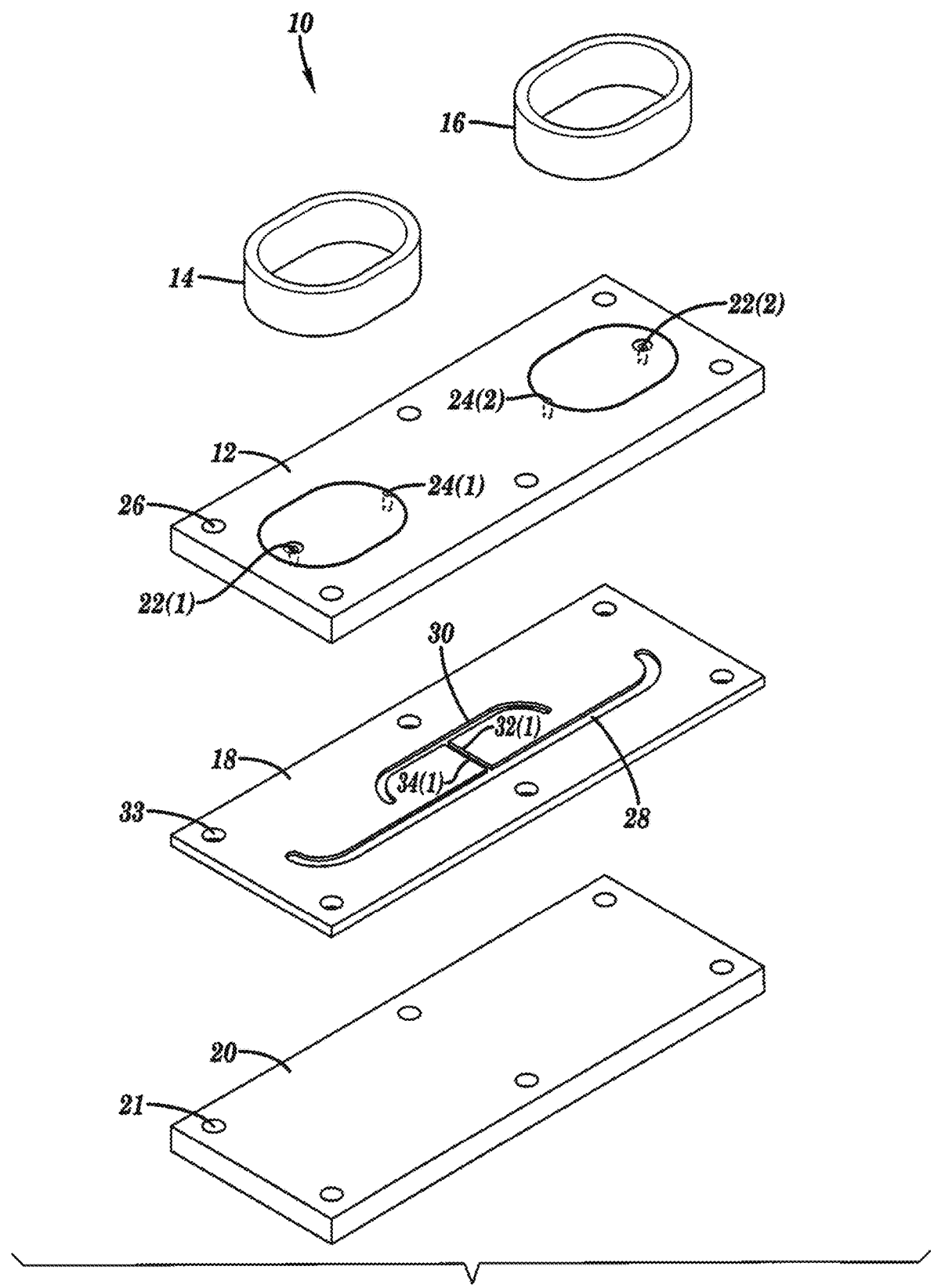
FIG. 1C is an exploded view of the device of the present application.
Figure 1D:
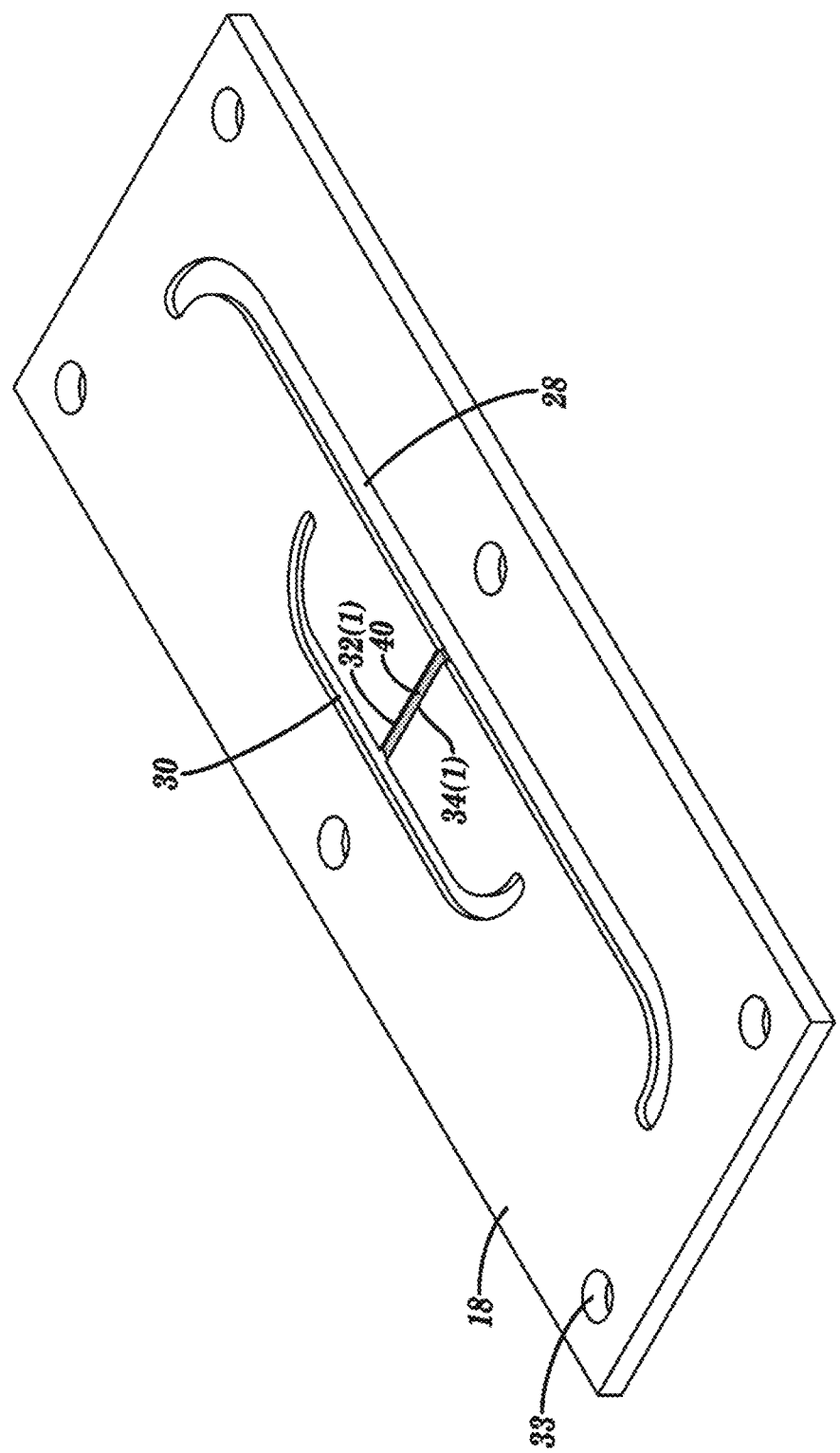
FIG. 1D is a perspective view of the channel layer of the device shown in FIGS. 1B and 1C with a catalyst seeded in a channel of the channel network.

FIGS. 1A-1C are schematic, top, and exploded views of a first embodiment of device 10 of the present application. Device 10 includes reservoir base 12, first reservoir 14, second reservoir 16, channel layer 18, and base 20, although device 10 may include other types and or numbers of elements or components, such as additional fluidic components or sealing gaskets, in other combinations. In one embodiment, device 10 is a microfluidic device for manipulating or controlling fluids in the range of microliters to picoliters, although device 10 may be used on any scale.

The elements of device 10, as described above, are formed from a biocompatible thermoplastic, such as polymethyl methacrylate (PMMA), polycarbonate, polystyrene, polyester, polyethylene, polyvinyl chloride, cyclic olefin copolymer, polypropylene, polyurethane, or polyetheretherketon (PEEK), or combinations thereof, although the elements of device 10 may be formed of other materials such as silicone including polydimethylsiloxane (PDMS), glass, or metals, or combinations thereof. In this embodiment, device 10 is made of a transparent material such that channel layer 18 is visible in the top view as shown in FIG. 1B, although opaque materials may be utilized. According to one embodiment, the elements of device 10 are formed using 3-D printing, although the elements of device 10 may be formed using other methods, such as injection molding.

Reservoir base 12 includes inlets 22(1) and 22(2) and outlets 24(1) and 24(2) that extend through reservoir base 12. Outlets 24(1) and 24(2) are positioned closer to the center of reservoir base 12 than inlets 22(1) and 22(2). Inlet 22(1) and outlet 24(1) are positioned to be associated with first reservoir 14, while inlet 22(2) and outlet 24(2) are positioned to be associated with second reservoir 16. In one embodiment, reservoir base 12 includes threaded holes 26 that allow reservoir base 12 to be coupled using threaded screws 35, as shown in FIG. 1B, to the other elements of device 10 as described below. Reservoir base 12 is shown as having a rectangular configuration. However, reservoir base 12 may have any other shapes such as circular or square, by way of example only.

First reservoir 14 is positioned on reservoir base 12 to be associated with inlet 22(1) and outlet 24(1), while second reservoir 16 is positioned on reservoir base 12 to be associated with inlet 22(2) and outlet 24(2). In one embodiment, first reservoir 14 and second reservoir 16 are coupled to reservoir base 12 by one of an adhesive, chemical bonding, or hot embossing. In another embodiment, first reservoir 14 and second reservoir 16 may be integrally formed on reservoir base 16. First reservoir 14 and second reservoir 16 are configured to hold a volume of liquid therein, and may be scaled depending on the application. In one embodiment, reservoir base 12 includes threaded holes 26 that allow reservoir base 12 to be coupled using threaded screws to the other elements of device 10 as described below. First reservoir 14 and second reservoir 16 are in fluid communication with channel layer 18 through inlets 22(1) and 22(2) and outlets 24(1) and 24(2) when reservoir base 12 is coupled to channel layer 18. First reservoir 14 and second reservoir 16 are open access reservoirs which allows access to the fluid during operation.

Figure 2:
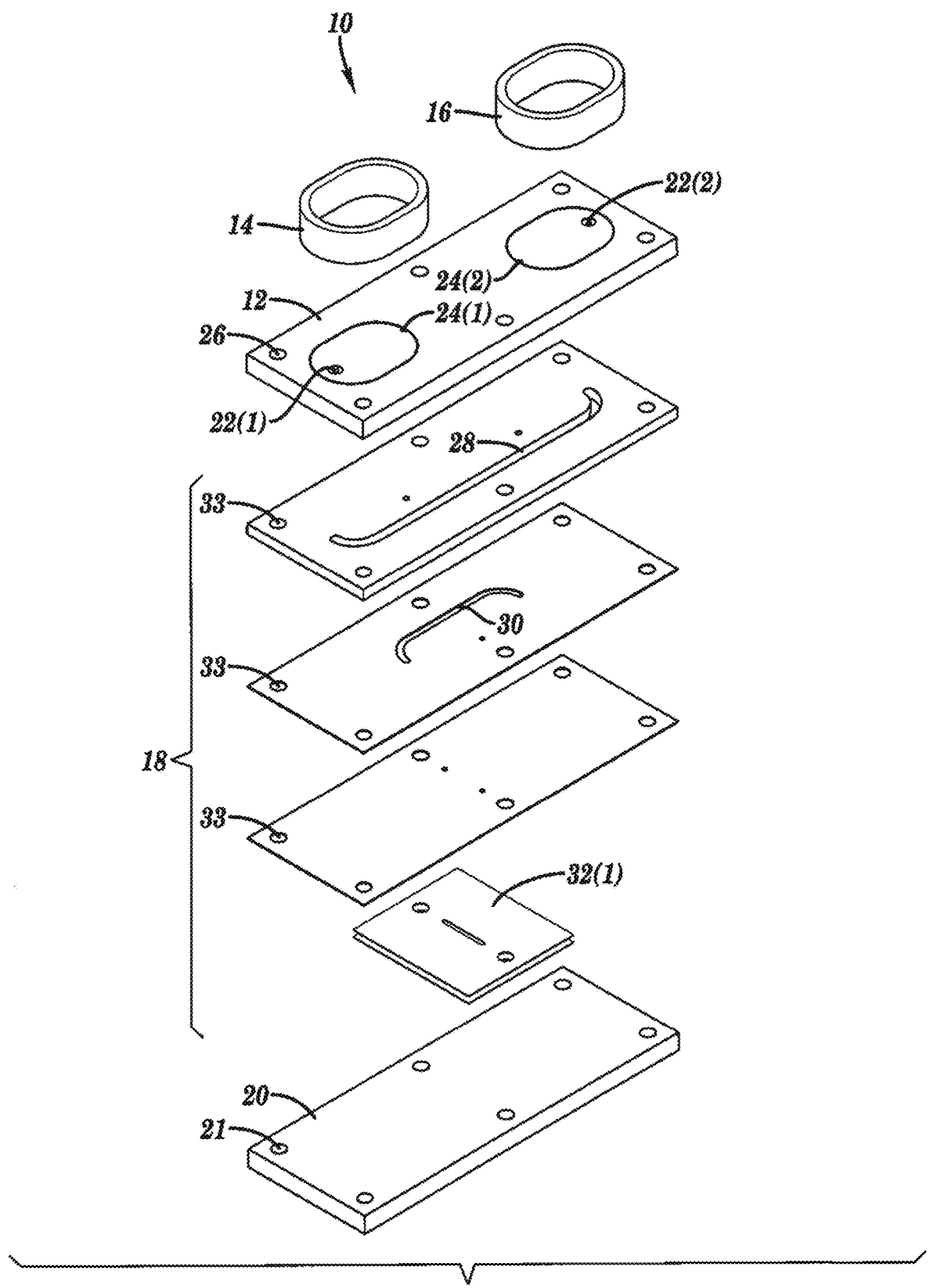
FIG. 2 is an exploded view of another embodiment of the device of the present application with a channel layer made up of multiple layers.
Figure 4:
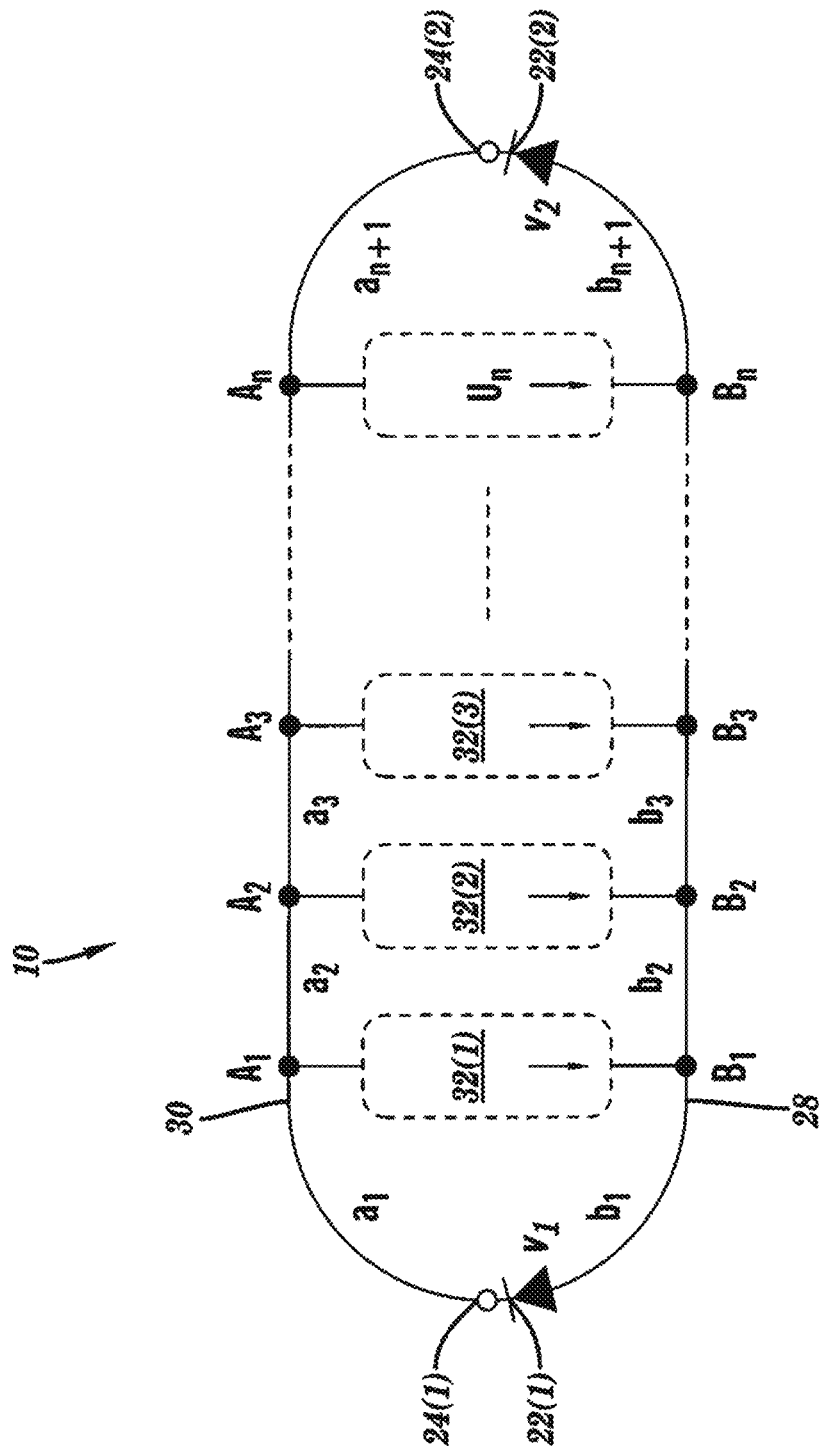
FIG. 4 is a schematic view of the device of the present application with multiple channel networks.

Channel layer 18 includes inlet channel 28, outlet channel 30, and channel network 32(1), although channel layer 18 may include other fluidic channels in other configurations, such as additional channel networks as shown in FIG. 4. In one embodiment, inlet channel 28, outlet channel 30, and channel network 32(1) are laser etched into a surface of channel layer 18, although in other embodiments inlet channel 28, outlet channel 30, and channel network 32(1) may be formed within channel layer 18 by 3-D printing, by way of example. In this embodiment, channel layer 18 is a single layer of material that includes inlet channel 28, outlet channel 30, and channel network 32(1). In another embodiment, inlet channel 28, outlet channel 30, and channel network 32(1) are formed on separate layers, as shown in FIG. 2. In one embodiment, channel layer 18 includes threaded holes 33 that allow channel layer 18 to be aligned with and coupled to reservoir base 12 using threaded screws 35 as shown in FIG. 1B.

In this embodiment, channel layer 18 is coupled directly to reservoir base 12, although in other embodiments additional materials, such as sealing gaskets by way of example, may be located between channel layer 18 and reservoir base 12. When channel layer 18 is coupled to reservoir base 12, inlet channel 28 is in fluid communication with inlet 22(1) of first reservoir 14 and inlet 22(2) of second reservoir 16. Outlet channel 30 is in fluid communication with outlet 24(2) of first reservoir 14 and outlet 24(2) of second reservoir 16.

Channel network 32(1) includes channel 34(1) extending between inlet channel 28 and outlet channel 30. In another embodiment, channel network 32(1) may include plurality of channels 34(1)-34(n), as described below. In one embodiment, channel 34(1) is configured to provide a flow rate of the first and second flows of fluid to channel 34(1) to simulate a ratio of physiological perfusion rates in an organ, as known in the art.

Base 20 is configured to support channel layer 18. Base 20 includes threaded holes 21 configured to align base 20 to channel layer 18 and reservoir base 12. Base 20 is coupled to channel layer 18 and reservoir base 12 by threaded screws 35 as shown in FIG. 1B. Base 20 allows for the sealing of channel layer 18 within device 10.

Figure 3A:
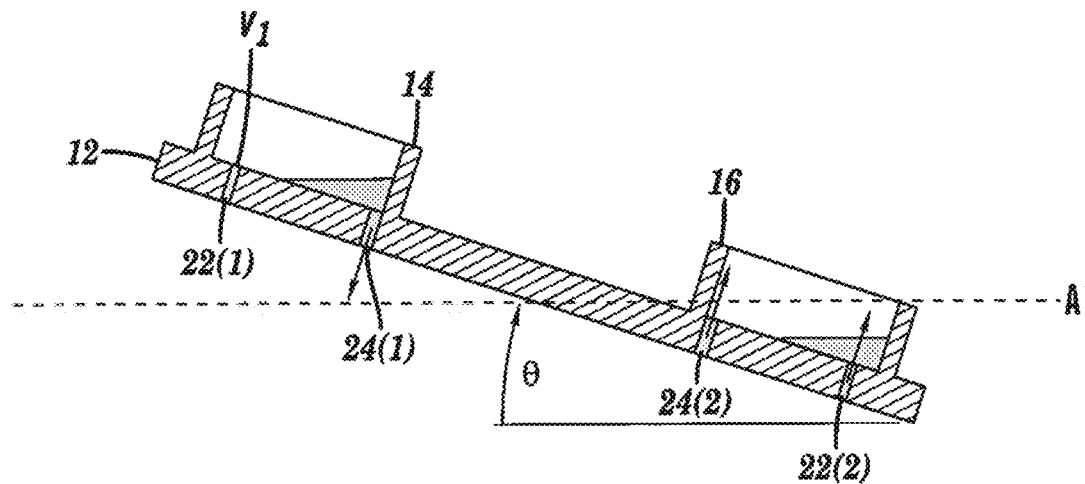
FIG. 3A is a side cross-sectional view of a reservoir base and associated reservoirs of the device of the present application in a forward tilted position.

Device 10 is configured to provide unidirectional flow of fluid through channel network 32(1). As shown in FIGS. 3A-3D, outlets 24(1) and 24(2) of first reservoir 14 and second reservoir 16, respectively, are located closer to horizontal axis (A), about which the device is tilted between the forward tilted position and the reverse tilted position as shown in FIGS. 3A and 3C, than the inlets 22(1) and 22(2) of first reservoir 14 and second reservoir 16, respectively. As a result, the first and second flows of fluid traverse channel network 32(1) in the same direction when device 10 is moving between the forward tilted and the reverse tilted positions, as described below. In one embodiment, the first and second flows of fluid provide a continuous flow of fluid across channel network 32(1) when device 10 is moving between the forward tilted and reverse tilted positions, as described below.

Figure 3B:
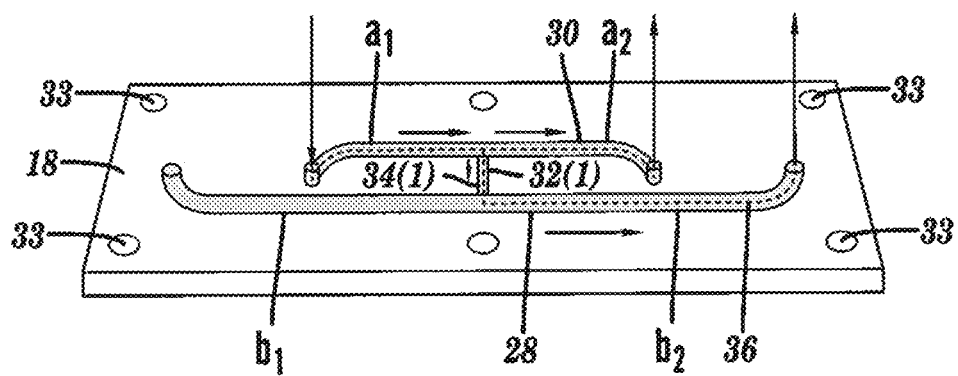
FIG. 3B is a perspective view of a channel layer of the device of the present application illustrating a first fluid circuit formed when the device is in the forward tilted position shown in FIG. 3A.
Figure 3C:
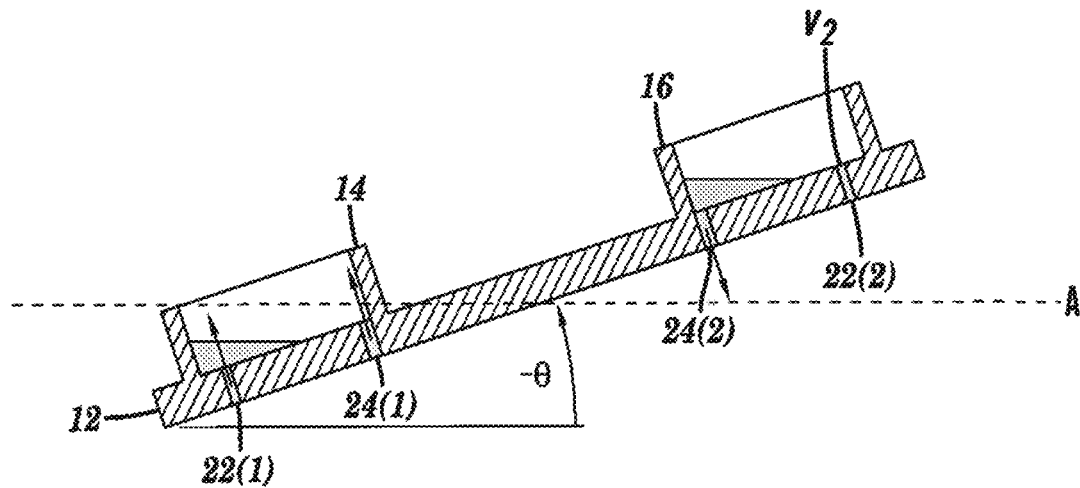
FIG. 3C is a side cross-sectional view of the reservoir base and associated reservoirs of the device of the present application in a reverse tilted position.

Referring now to FIGS. 3A and 3B, when device is tilted at angle $\Theta$ in a forward tilted position at angle $\Theta$, as shown in FIG. 3A, with respect to horizontal axis A, first fluid circuit 36 is formed for directing a first flow of fluid from outlet 24(1) of first reservoir 14, through outlet channel 30, through channel network 32(1), through inlet channel 28, to the both inlet 22(2) and outlet 24(2) of second reservoir 16. The first flow of fluid traverses channel network 32(1) in a direction from outlet channel 30 to inlet channel 28. Inlet 22(1) and outlet 24(1) of first reservoir 14 are positioned to prevent fluid flow to inlet 22(1) of first reservoir 14 when device 10 is in the forward tilted position. In this position, inlet 22(1) provides a passive valve $V_1$. An air-liquid interface is formed at inlet 22(1) that halts fluid flow in portion $b_1$ of inlet channel 28 based on capillary force at inlet 22(1).

Figure 3D:
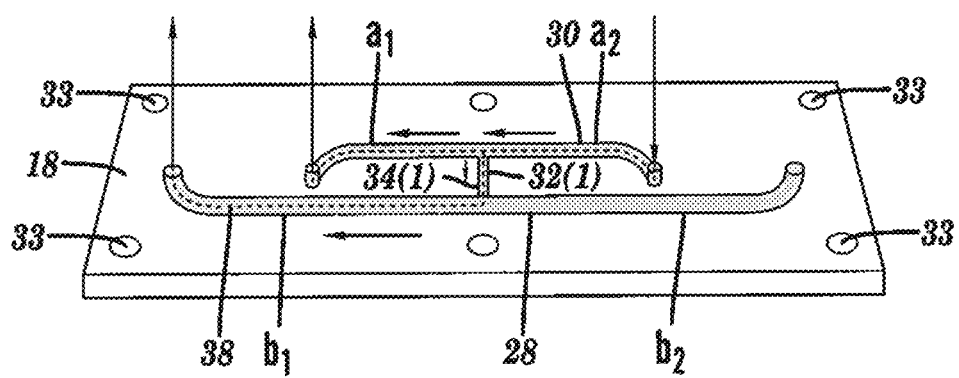
FIG. 3D is a perspective view of the channel layer of the device of the present application illustrating a second fluid circuit formed when the device is in the reverse tilted position shown in FIG. 3C.

Referring now to FIGS. 3C and 3D, when the device is tilted in a reverse tilted position at angle $(-\Theta)$, as shown in FIG. 3C with respect to horizontal axis A, second fluid circuit 38 is formed for directing a second flow of fluid from outlet 24(2) of second reservoir 16, through outlet channel 30, through channel network 32(1), through inlet channel 28, to the both inlet 22(1) and outlet 24(1) of first reservoir 14. The second flow of fluid traverses channel network 32(1) in a direction from outlet channel 30 to inlet channel 28. Inlet 22(2) and outlet 24(2) of second reservoir 16 are positioned to prevent fluid flow to inlet 22(2) of second reservoir 16 when device 10 is in the reverse tilted position. In this position, inlet 22(2) provides a passive valve $V_2$. An air-liquid interface is formed at inlet 22(2) that halts fluid flow in portion $b_2$ of inlet channel 28 based on capillary force at inlet 22(2).

Device 10 also provides a backflow-proof mechanism to maintain unidirectional flow in channel network 32(1). This is shown in FIG. 4, which is a schematic view of device 10 of the present application. In this embodiment, device 10 includes plurality of channel networks 32(1)-32(n). Each of plurality of channel networks 32(1)-32(n) includes at least one fluid channel, but may include a plurality of channels as described below. Fluid channels within each channel network 32(1)-32(n) may have various configurations depending on the application. Channel networks 32(1)-32(n) each extend between input channel 28 and output channel 30. Each of channel networks 32(1)-32(n) includes an inlet and outlet labelled "$A_i$" and "$B_i$", respectively, where i=1 to n. Device 10 is configured such that fluid flow in each of channel networks 32(1)-32(n) is unidirectional from $A_i$ to $B_i$.

The connection portions of outlet channel 30 between the inputs $A_1$ to $A_n$ of each of channel networks 32(1)-32(n) are labeled "$a_1$", "$a_2$", . . . , and "$a_{n+1}$" (n≥0, integer). Output channel 30 has a hydraulic resistance of $R_{a_j}$, where j=1, 2, . . . , n+1. The connection portions of inlet channel 30 between the outputs $B_1$ to $B_n$ of each of channel networks 32(1)-32(n) are labeled "$b_1$", "$b_2$", . . . , and "$b_{n+1}$" (n≥0, integer). Input channel 28 has a hydraulic resistance of $R_{b_j}$, where j=1, 2, . . . , n+1. Portions of input channel $b_1$ and $b_{n+1}$ each contain at least one valve device $V_1$ and $V_2$, respectively. Device 10 utilizes passive valves based on capillary forces, but other valves that can open or close, or change the hydraulic resistance of specific channels may be utilized, such as check valves and multi-way valves, by way of example. $R_{b_i}^+$ is the overall hydraulic resistance of $b_i$ (i=1, n+1) when fluid flows towards the neighboring inlet 22(1) or 22(2) and $R_{b_i}^-$ is the overall hydraulic resistance when fluid flows away from the neighboring inlet 22(1) or 22(2). The hydraulic resistance $R_{b_i}^+ < R_{b_i}^-$.

Device 10 maintains continuous unidirectional flow ($A_i \rightarrow B_i$ with no backflow) during recirculating flow when Equation (1) is satisfied.

$$\frac{R_{a_1}}{R_{b_i}^+} = \frac{R_{a_j}}{R_{b_j}} = \ldots = \frac{R_{a_{n+1}}}{R_{b_{n+1}}^+}, j = 1, 2, \ldots, n+1; \quad (1)$$

The input channel 28, output channel 30, and channel networks 32(1)-32(n) of device 10 can otherwise be of any length and shape (such as rectangular, trapezoidal, circular, or irregular shapes). Under such design constraints, even when the valve devices $V_1$ and $V_2$ fail to fully limit backwards flow unidirectional flow across channel networks 32(1)-32(n) is maintained. For example, if during a transition period in a recirculating flow, $R_{b_i}^-$ drops close to $R_{b_i}^+$ (i=1 or n+1), the flow in channel networks 32(1)-32(n) will approach 0, but flow will not occur from $B_i$ to $A_i$, i.e. no backwards flow occurs in the channel networks 32(1)-32(n).

The unidirectional flow of device 10 can be used to deliver fluid to catalyst 40 located in one or more of plurality of channels 34(1)-34(n) of channel network 32(1). In one embodiment, catalyst 40 comprises a cell culture that serves as a biocatalyst for a biological reaction, although other biocatalysts, such as enzymes, may be utilized. Yet another alternative for catalyst 40 would be a chemical compound that serves as a non-biological catalyst for a chemical reaction. The cell culture may be at least one of liver cells, kidney cells, gastrointestinal tract cells, lung cells, skin cells, brain cells, bone marrow cells, heart cells, endothelial cells, skeleton muscle cells, pancreatic cells, adipocytes, neural cells, spleen cells, or adrenal cells, by way of example. In one embodiment, the cell culture includes cancerous cells. As set forth above, the channel 34(1) is configured to provide a flow rate of the first and second flows of fluid to channel 34(1) in a ratio to simulate a ratio of physiological perfusion rates in an organ, as known in the art, and may be designed based on the particular cell culture.

Figure 5A:
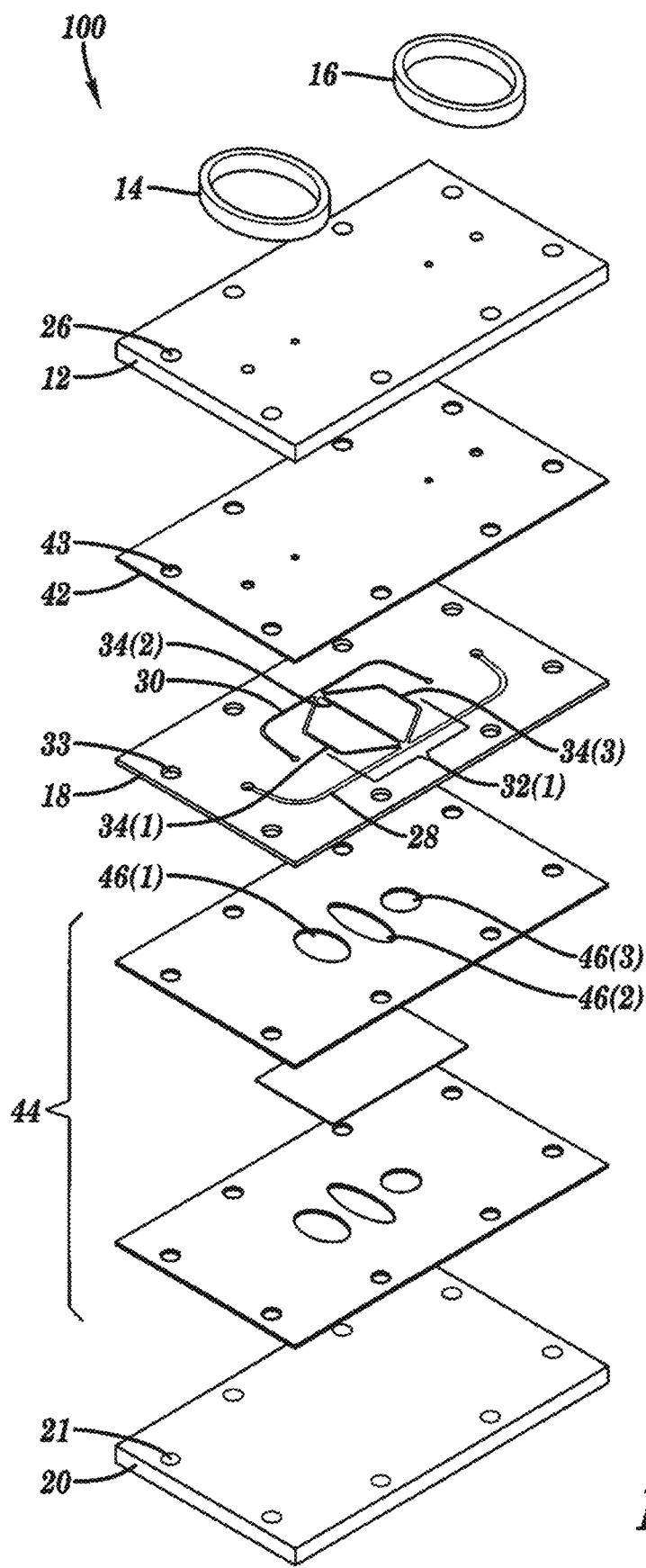
FIG. 5A is an exploded view of another embodiment of the device of the present application including a channel network with multiple channels.
Figure 5B:
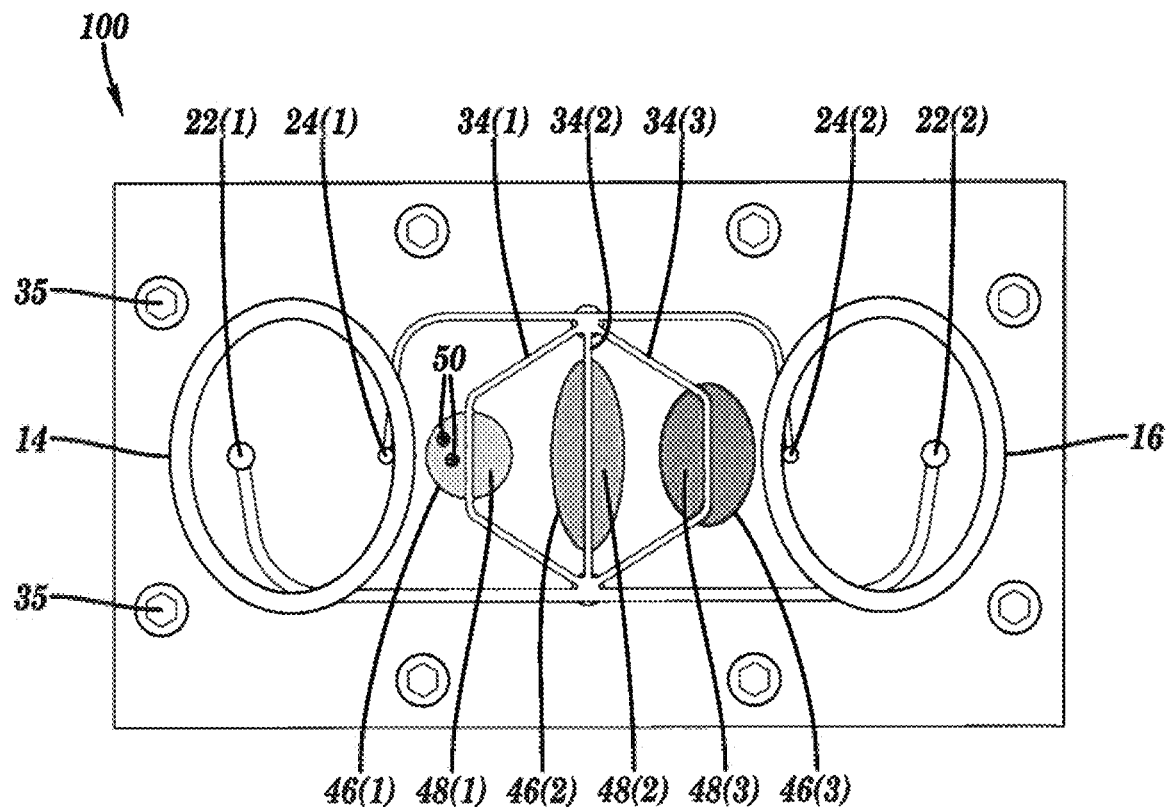
FIG. 5B is a top view of the device shown in FIG. 5A.

FIGS. 5A-5B are, respectively, an exploded view and a top view of another embodiment of the present application. Device 100 is the same in structure and operation as device 10 except as described below.

Figure 5C:
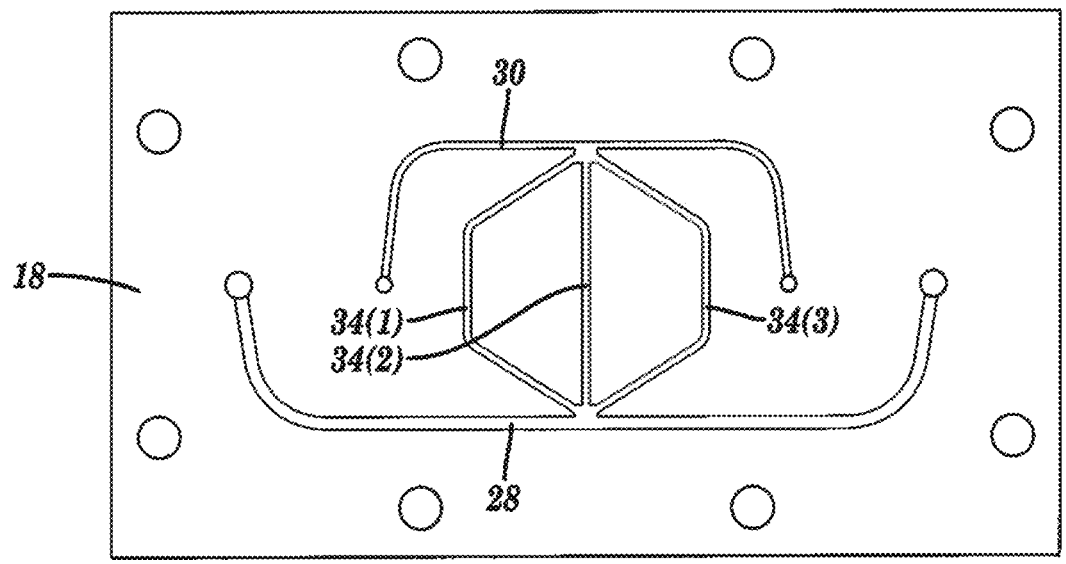
FIG. 5C is a top view of the channel layer of the device shown in FIG. 5A.

FIG. 5C is a top view of channel layer 18 of device 100. In this embodiment, channel layer 18 has channels 34(1)-(3) in channel network 32(1). Optional sealing gasket 42 is located between reservoir base 12 and channel layer 18. Sealing gasket 42 includes threaded holes 43 configured to align sealing gasket 42 to channel layer 18 and reservoir base 12. Sealing gasket 42 is coupled to channel layer 18 and reservoir base 12 by threaded screws 35 as shown in FIG. 5B.

In this embodiment, device 10 further includes optional insert 44. Optional insert 44 includes chambers 46(1)-46(3) configured to house individual cell cultures, although in other embodiments optional insert 44 may house other catalysts. Optional insert 44 allows for seeding cell cultures, although in other embodiments the cell cultures can be seeded directly in the channels of channel network 32(1), as described above. Chamber 46(1) is in fluid communication with channel 34(1) of channel network 32(1) to deliver the first and second flows of fluid across chamber 46(1), chamber 46(2) is in fluid communication with channel 34(2) of channel network 32(1) to deliver the first and second flows of fluid across chamber 46(2), and chamber 46(3) is in fluid communication with channel 34(3) of channel network 32(1) to deliver the first and second flows of fluid across chamber 46(3).

Channel 34(1) is configured to provide a first flow rate of first and second flows of fluid to chamber 46(1), channel 34(2) is configured to provide a second flow rate of the first and second flows of fluid to chamber 46(2), and channel 34(3) is configured to provide a third flow rate of the first and second flows of fluid to chamber 46(3). In this embodiment, the first flow rate, the second flow rate, and the third flow rate are in a ratio configured to simulate the ratio of physiological perfusion rates in a colon, a liver, and in bone marrow, respectively, although other ratios for simulating other physiological perfusion rates in other organs may be employed. In this embodiment, chamber 46(1) is seeded with colon cell culture 48(1), chamber 46(2) is seeded with liver cell culture 48(2), and chamber 46(3) is seeded with bone marrow cell culture 48(3), although other cell cultures may be utilized in other combinations. In one embodiment, colon cell culture may include cancerous cells 50 therein.

Another aspect of the present application relates to a method for delivering a fluid to a catalyst. This method includes providing the device of the present application and providing the catalyst in the at least one channel of the channel network. A fluid is provided in at least one of the first reservoir or the second reservoir. The fluid is delivered to the at least one channel of the channel network through the first and second fluid circuits by alternately tilting the device between the forward tilted position and the reverse tilted position, with respect to the horizontal axis, respectively, to deliver the fluid to the catalyst located therein.

First device 10 according to the present application is provided. Device 10 is provided with channel layer 18 having channel network 32(1). Channel network 32(1) includes channel 34(1), although in other embodiments, central network may include a plurality of channels. Channel 34(1) is sized to provide a desired flow rate across channel 34(1). In one embodiment, channel 34(1) is configured to provide a flow rate of the first and second flows of fluid to channel 34(1) to simulate a physiological perfusion rate in an organ, by way of example. In another embodiment, device 10 may include plurality of channels 34(1)-34(n) in channel network 32(1). Each of plurality of channels 34(1)-34(n) may be configured to provide a different flow rate. Plurality of channels 34(1)-34(n) may provide flow rates in a ratio to mimic the ration of physiological perfusion rates in various organs.

Catalyst 40 is provided in channel 34(1) of the channel network 32(1). In another embodiment, catalyst 40 may be provided in insert 44 as shown in FIG. 5A. Catalyst 40 may be any substance that may react to a fluid passed over the substance. In one embodiment, catalyst 40 comprises a cell culture including at least one of liver cells, kidney cells, gastrointestinal tract cells, lung cells, skin cells, brain cells, bone marrow cells, heart cells, endothelial cells, skeleton muscle cells, pancreatic cells, adipocytes, neural cells, spleen cells, or adrenal cells. In one embodiment, catalyst 40 may include cancerous cells for determining the efficacy of a chemotherapy treatment.

Next, device 10 is assembled. Device 10 may be assembled by inserting threaded screws 35 through the corresponding threaded holes 26, 33, and 21 in reservoir base 12, channel layer 18, and base 20, respectively, although device 10 may be assembled using other techniques. Reservoirs 14 and 16 remain open for the exchange of gas and nutrients, while the rest of the device is hydraulically sealed. In another embodiment, a gas permeable membrane may be placed over reservoirs 14 and 16. Once the device is assembled, a fluid is provided in first reservoir 14 and second reservoir 16. The fluid may be any fluid of interest for interacting with catalyst 40. In one embodiment, the fluid may include a drug substance for testing the impact of the drug substance on catalyst 40, such as a cell culture.

Next, the fluid is delivered to channel 34(1) of channel network 32(1) through the first and second fluid circuits 36, 38, as shown in FIGS. 3B and 3D, respectively, as described above. The fluid is delivered to channel 34(1) by alternately tilting device 10 between the forward tilted position shown in FIG. 3A and the reverse tilted position shown in FIG. 3C, with respect to the horizontal axis A, respectively, to deliver the fluid to catalyst 40 located therein. Alternately tilting device 10 allows the fluid to be delivered by gravity, although in other embodiments a pump may be utilized to deliver the fluid. In one embodiment device 10 is tilted between approximately one degree to approximately 45 degrees about the horizontal axis A. In one embodiment, device 10 is tilted about 18 degrees about horizontal axis A. The tilting may be performed by placing device 10 on a rocker platform device, by way of example.

First fluid circuit 36, as shown in FIG. 3B, is formed when device 10 is in the forward tilted position as shown in FIG. 3A. First fluid circuit 36 delivers a flow of fluid from outlet 24(1) of first reservoir 14, through outlet channel 30, through channel network 32(1), through inlet channel 28, to the both inlet 22(2) and outlet 24(2) of second reservoir 16. The first flow of fluid traverses channel network 32(1) in a direction from outlet channel 30 to inlet channel 28. Fluid flow to inlet 22(1) of first reservoir 14 is prevented when device 10 is in the forward tilted position. In this position, an air-liquid interface is formed at inlet 22(1) that provides a passive valve $V_1$ that halts fluid flow in portion $b_1$ of inlet channel 28 based on capillary force at inlet 22(1).

Second fluid circuit 38, as shown in FIG. 3D, is formed when device 10 is in the reverse tilted position as shown in FIG. 3C with respect to horizontal axis (A). Second fluid circuit delivers a second flow of fluid from outlet 24(2) of second reservoir 16, through outlet channel 30, through channel network 32(1), through inlet channel 28, to the both inlet 22(1) and outlet 24(1) of first reservoir 14. The second flow of fluid traverses channel network 32(1) in a direction from outlet channel 30 to inlet channel 28, i.e., the same direction as in the forward tilted position. Fluid flow to inlet 22(2) of second reservoir 16 is prevented when device 10 is in the reverse tilted position. In this position, an air-liquid interface is formed at inlet 22(2) that provides a passive valve $V_2$ that halts fluid flow in portion $b_2$ of inlet channel 28 based on capillary force at inlet 22(2).

Device 10 provides the first and second flows of fluid to channel 34(1) of channel network 32(1) in the same direction when the device is moving between the forward tilted and the reverse tilted positions. Device 10 is further configured so that backflow through channel 34(1) of channel network 32(1) is prevented. In one embodiment, device 10 provides a continuous flow of the first and second flows of fluid across channel network 32(1) when device 10 is moving between the forward tilted and reverse tilted positions.

A further aspect of the present application relates to a method for delivering a fluid to a cell culture. This method includes seeding a cell culture in a device comprising a channel layer comprising one or more inlet channels, one or more outlet channels, and a channel network comprising at least one channel extending between the one or more inlet channels and the one or more outlet channels. The channel layer is fluidly coupled to a first reservoir and a second reservoir. Each of the first reservoir and the second reservoir have an inlet and an outlet such that the inlets of the first and second reservoirs are in fluid communication with the one or more inlet channels and the outlets of the first and second reservoirs are in fluid communication with the one or more outlet channels. When the device is tilted in a forward tilted position, with respect to a horizontal axis, a first fluid circuit is formed for directing a first flow of fluid from the outlet of the first reservoir, through the one or more outlet channels, through the channel network, through the one or more inlet channels, to both the inlet and the outlet of the second reservoir. When the device is tilted in a reverse tilted position, with respect to the horizontal axis, a second fluid circuit is formed for directing a second flow of fluid from the outlet of the second reservoir, through the one or more outlet channels, through the channel network, through the one or more inlet channels, to both the inlet and the outlet of the first reservoir. The outlets of the first reservoir and the second reservoir are located closer to the horizontal axis, about which the device is tilted between the forward tilted position and the reverse tilted position, than the inlets of the first reservoir and the second reservoir, respectively. A fluid is provided in at least one of the first reservoir or the second reservoir. The fluid is delivered to the cell culture through the first and second fluid circuits by alternately tilting the device between the forward tilted position and the reverse tilted position, with respect to the horizontal axis, respectively.

Yet another aspect of the present application relates to a method for testing metabolism dependent chemotherapeutic toxicity. This method includes seeding a colon cell culture comprising cancerous cells in a first cell culture chamber of a cell culture insert, a liver cell culture in a second cell culture chamber of the cell culture insert, and a bone marrow cell culture in a third cell culture chamber of the cell culture insert. The cell culture insert is fluidly coupled to a channel layer comprising one or more inlet channels, one or more outlet channels, and a channel network comprising a first channel, a second channel, and a third channel arranged in parallel configuration and extending between the one or more inlet channels and the one or more outlet channels such that the first cell culture chamber is in fluid communication with the first channel, the second cell culture chamber is in fluid communication with the second channel, and the third cell culture chamber is in fluid communication with the third channel. The channel layer is positioned in fluid communication with a reservoir base having a first reservoir and a second reservoir positioned at opposing ends thereof. Each of the first reservoir and the second reservoir have an inlet and an outlet extending through the reservoir base such that the inlets of the first and second reservoirs are in fluid communication with the one or more inlet channels and the outlets of the first and second reservoirs are in fluid communication with the one or more outlet channels. The cell culture insert, channel layer, and the reservoir base are assembled to form a device. When the device is tilted in a forward tilted position, with respect to a horizontal axis, a first fluid circuit is formed for directing a first flow of fluid from the outlet of the first reservoir, through the one or more outlet channels, through the channel network, through the one or more inlet channels, to both the inlet and the outlet of the second reservoir. When the device is tilted in a reverse tilted position, with respect to the horizontal axis, a second fluid circuit is formed for directing a second flow of fluid from the outlet of the second reservoir, through the one or more outlet channels, through the channel network, through the one or more inlet channels, to the inlet of the first reservoir. The outlets of the first reservoir and the second reservoir are located closer to the horizontal axis, about which the device is tilted between the forward tilted position and the reverse tilted position, than the inlets of the first reservoir and the second reservoir, respectively. A fluid is provided in at least one of the first reservoir or the second reservoir. The fluid is delivered to the first, second, and third cell culture chambers through the first and second fluid circuits by alternately tilting the device between the forward tilted position and the reverse tilted position, with respect to the horizontal axis, respectively.

EXAMPLES

Example 1—Materials and Methods

1) System Construction

The UniChip for demonstration has a microfluidic circuit (FIGS. 6A-B) comprising a pair of open-access reservoirs, a cell perfusion channel ("Cu"), and supporting channels ("a1", "a2", "b1" and "b2") with two integrated passive valves ("v1" and "v2").

Rapid prototype UniChips were fabricated mainly in poly(methyl methacrylate) (PMMA) using laser ablation and solvent assisted bonding techniques. The UniChip device consists of a top and a bottom pieces with a cell insert and two side sealing sets sandwiched in between (FIG. 6D). The top piece contains reservoirs and supporting channels and was made from five PMMA layers (FIG. 6C): (i) reservoir walls; (ii) a reservoir base layer with openings connecting reservoirs to the supporting channels; (iii) b1/b2 channel layer (channel size: 1.4 mm×1.5 mm×26.3 mm, width×depth×length); (iv) a1/a2 channel layer (1.3 mm×0.25 mm×15.3 mm); and (v) a channel seal layer with openings connecting to the perfusion channel. All layers were cut and patterned from PMMA sheets (6 mm, 3 mm, or 1.5 mm thickness, McMaster, Elmhurst, Ill.; 0.25 mm thickness, Goodfellow, Coraopolis, Pa.) with a CO2 laser (VersaLaser VLS3.50, the Universal Laser Systems, Scottsdale, Ariz.). Layers (ii)-(v) were permanently bonded together via ethanol assisted thermal bonding, as discussed in A. M. Wan, et al., *J Vis Exp,* 2017, DOI: 10.3791/55175, the disclosure of which is incorporated herein by reference. Briefly, a thin layer of ethanol was applied to the bonding interface. PMMA layers were then aligned, placed into a preheated hot press (70° C.), and held together with 1.2 MPa pressure for 2 min. Reservoir walls were glued onto the reservoir base with a weld-on acrylic solvent cement (SCIGRIP, Durham, N.C.) to complete the top piece (FIG. 6D). The bottom piece of the housing was also cut from PMMA sheets (6 mm) using laser ablation, and installed with screw-to-expand inserts for chip assembly.

The cell insert to accommodate endothelial cell cultures comprised a silicone perfusion channel layer with channel size of 0.76 mm×0.25 mm×6.25 mm (width×depth×length) and a cell culture coverslip (FIG. 6D). The two sealing sets aside also comprised a silicone layer and a plastic coverslip. These silicone layers and the coverslips were patterned with the $CO_2$ laser from 0.25 mm thick silicone sheets (Grace Bio-Labs, Bend, Oreg.) and Thermanox plastic coverslips (Thermo Fisher, Waltham, Mass.), respectively. They were sterilized in 70% ethanol in DI water, aligned and assembled, and dried before used for experiment.

The BiChip to provide bidirectional perfusion over cells contains three separate microfluidic circuits (FIG. 6E). Each consists of a pair of reservoirs and a perfusion channel with the central segment of the same size as that of the perfusion channel in the UniChip. The housing and the cell insert were fabricated and prepared with the same materials and techniques as used for the UniChips.

Static control chips were assembled from a UniChip cell insert and a silicone ring, which were the reservoir walls of static chips and patterned with the $CO_2$ laser from a 2 mm thick silicone sheet. All parts were sterilized in 70% ethanol in DI water, aligned and assembled, and dried before used for experiment.

2) Microfluidic Channel Design

The fluid flows on the UniChips and the BiChips are driven by gravity. The volumetric flow rate (Q) of a microfluidic channel follows Equation (2), where $\Delta P$ and R are the pressure drop and the hydrodynamic resistance, respectively.

$$Q = \frac{\Delta P}{R} \quad (2)$$

The dimensions of microfluidic channels, including the perfusion and the supporting channels, were designed to achieve desired shear stress and flow rate in the perfusion channel of the UniChip. When the UniChip is placed on a tilted platform (e.g. +18°), valve $v_1$ is closed, and flow in channel $b_1$ is halted (FIG. 6B). The flow rates in the other channels followed Equation set (3), where $\Delta P_{I_a I_a}$ is the pressure drop between I/O ports, $I_1$ and $I_3$; and $\Delta P_{I_a I_a}$ is that between $I_1$ and $I_4$ (FIG. 6B). The pressure drops ($\Delta P$) were determined by the height difference ($\Delta h$) between the top surface of fluid at the inlet and the outlet and can be calculated by Equation (4), where $\rho$ and $g$ are fluid density and the gravity constant, respectively. The hydrodynamic resistance for rectangular channels was estimated by Equation (5), where μ is the dynamic fluid viscosity; l, w, and h (h<w) are the length, width and height of the channel, respectively. The resistance for the short tubular section at the entrance and exit connecting to the reservoirs was estimated by Equation (6), where r and L are the radius and the length, respectively. Yet their resistance is usually negligible compared to the rest of the channel. For the desired Q and shear stress τ, channel dimensions were chosen to satisfy Equations (3)-(7). The microfluidic channels on the BiChip controls were designed in the same way.

$$\begin{cases} \Delta P_{l_1 l_3} = Q_{a_1} \cdot R_{a_1} + Q_{a_2} \cdot R_{a_2} \\ \Delta P_{l_1 l_4} = Q_{a_1} \cdot R_{a_1} + Q_{C_u} \cdot (R_{C_u} + R_{b_2}) \\ Q_{a_1} = Q_{a_2} + Q_{C_u} \end{cases} \quad (3)$$

$$\Delta P = \rho g \Delta h \quad (4)$$

$$R_{rectangular} = \frac{12\,\mu l}{w h^3}\left[1 - \frac{192h}{\pi^5 w}\tanh\left(\frac{\pi w}{2h}\right)\right]^{-1} \quad (5)$$

$$R_{tubular} = \frac{8\,\mu L}{\pi r^4} \quad (6)$$

$$\tau = \frac{6\mu Q}{w h^2} \quad (7)$$

3) Fluid Dynamics Simulation and Characterization

The fluid dynamics in the demonstration UniChip devices and the BiChip controls were simulated in 3D using COMSOL Multiphysics to validate and optimize the microchannel design for the desired perfusion rate and wall shear stress. The Laminar Flow interface was used. Gravity was applied as the only volume force. The steady state incompressible Navier-Stokes equations were used to model the fluid flow. The flow rate and the shear stress were derived from the velocity results. The equation $\mu = 0.78 \times 10^{-3}$ Pa·s was used for culture medium at 37° C. The fluid dynamics were also characterized experimentally using colored food dyes for visualization. Flow velocities in different channels were determined by timing the passage of dyes. The experiments were conducted at room temperature (~20° C.), thus the results were corrected for fluid viscosity at room temperature ($\mu = 1.00 \times 10^{-3}$ Pa·s) before being compared to the designed or simulation values.

4) Cell Culture

Cryopreserved human umbilical vein endothelial cells (HUVECs) from Lonza (Walkersville, Md.) were recovered and expanded in Endothelial Cell Growth Medium-2 (EGM-2, Lonza) and maintained at 37° C. with 5% $CO_2$ in a humidified cell culture incubator. Cells were passaged at 80% confluence with TrypLE Express (Thermo Fisher) and used for experiments at passage 6. 1× Penicillin-Streptomycin (Thermo Fisher) was supplemented to culture medium for experiments.

5) Device Assembly and Operation

HUVEC cultures on cell inserts were first prepared in culture dishes (FIG. 6F). Cell culture area was coated with a mixture of collagen IV (50 μg/mL, Sigma-Aldrich, St. Louis, Mo.) and fibronectin (12.5 μg/mL, Sigma-Aldrich) in DPBS (Thermo Fisher), and incubated at 37° C. for 1 hour. The coating solution was then removed and the coated area was rinsed with DPBS. HUVECs were seeded onto cell inserts at density of 100 K/cm², and maintained in static culture dishes for 24 h to allow for cell settlement and attachment prior to transferring to the onchip systems. UniChips and the BiChips were assembled by sandwiching a cell-loaded insert between a top and a bottom pieces of the housing and securing with screws. Each reservoir was filled with 90 IA culture medium (180 μl per pair of reservoirs), and capped with lid made from breathable polyurethane membranes (Sigma-Aldrich) to minimize evaporation. The assembled Unichips and BiChip were placed on a rocking platform (Next Advance, Averill Park, N.Y.) that tilted at ±18° and flipped the tilt direction every 15 s. The whole system was placed inside a 5% $CO_2$ cell culture incubator. The static chips remained in static culture dishes with each reservoir filled with 180 μl culture medium. For all chips, medium was replenished daily.

6) Immunofluorescence Microscopy

Phase contrast micrographs of live cell morphology were acquired with an inverted microscope (Olympus) right before device assembly and daily after assembly for 5 days. Cells were then analyzed by immunofluorescence staining for VE-cadherin and actin filaments (F-actin). Staining was carried out at room temperature. Cells were fixed with Image-iT™ Fixative Solution (4% paraformaldehyde, Thermo Fisher) for 10 min, washed with DPBS (Thermo Fisher), permeabilized with 0.1% Triton X-100 (Sigma-Aldrich) in DPBS for 10 min, blocked with 5% bovine serum albumin (BSA) blocking buffer (Alfa Aesar, Haverhill, Mass.) for 1 hour, and then incubated with Alexa Fluor 488 conjugated VE-cadherin monoclonal antibody (4 μg/mL, Santa Cruz Biotechnology, Dallas, Tex.) and Cruzfluor 555 conjugated phalloidin (1 μg/mL, Santa Cruz Biotechnology) in 1% BSA for 2 hours. Samples were then washed 3 times in DPBS and mounted on slides with Fluoroshield™ with DAPI (Sigma-Aldrich) for nuclear counterstain. Images were captured with a Zeiss LSM 710 confocal microscope and analyzed in ImageJ. Visual orientation analysis on cell actin filaments was performed using an ImageJ directional analysis plugin—OrientationJ as described in E. Fonck, et al., *Stroke*, 2009, 40, 2552-2556, the disclosure of which is incorporated herein by reference in its entirety. Cells were counted based on nuclear staining.

7) Statistical Analysis

Data was presented as mean±SD. Multiple groups were analyzed by one-way ANOVA with Tukey's multiple comparisons test (GraphPad Prism). $p < 0.05$ was considered significant.

Example 2—Results and Discussion

1. Design and Operation of a Demonstration UniChipDevice on the Pumpless Platform A simple UniChip device used for demonstration is illustrated in FIGS. 6A-6B, where one UCN composed of a straight rectangular microfluidic channel was used as the perfusion channel (Cu), and a pair of reservoirs on a tilted rocking platform were used to provide reciprocating flow input (FIG. 1). Valves V1 and V2 were two 0.4 mm diameter tubular channels connecting reservoirs to channel b1 or b2 and operate passively by capillary forces. Briefly, when the pumpless platform is tilted clockwise by 18° a liquid-air interface forms in V1. The capillary force retains fluid in V1 if the elevation difference between two reservoirs does not exceed the capillary rise (h) it can support. Capillary rise h can be calculated from Equation (8), as set forth below:

$$h = 2\gamma \cos \theta / \mu g r \quad (8)$$

where r is the radius of a cylindrical channel, θ is the contact angle, and γ is the liquid-air surface tension.

Flow in channel b1 is thus halted. Gravity drives flow from Reservoir I to Reservoir II through channels a1, Cu, b2, and a2. Similarly, when the platform flips counterclockwise, a liquid-air interface forms in V2 and prevents backflow in channel b2. Fluid returns to Reservoir I though a2, Cu, b1, and a1. In both cases, the flow direction in channel Cu remains the same.

The dimensions of channels a1 and b1 were identical to those of a2 and b2, respectively. Such design met the requirements of Equation (1) set forth above, which prevented backflow in the perfusion channel in cases where the liquid-air interface formation in valves is delayed (e.g., excessive fluid in the reservoirs covers the valves) when the platform flips.

2) Computational and Experimental Analysis of Fluid Dynamics

Microfluidic channel dimensions were chosen to achieve desired flow rate and shear stress. To verify the channel design, the fluid dynamics of the demonstration UniChip were simulated through finite element analysis of the fluid velocity (FIG. 7A i). The flow rates and shear stress derived from the simulated velocity field closely matched the design values (FIG. 7A ii-iii). The maximum flow velocity at the center streamline for each channel in an operating device was experimentally determined by measuring the linear velocity of a moving dye front. After corrected for fluid viscosity difference (1.00×10−3 Pa·s for flow experiments at 20° C. vs. 0.78×10-3 Pa. s for culture at 37° C.), the velocity results of all channels were within ±1~4% of the simulated values (FIG. 7A iv). Together these results validated the design of UniChip channel dimensions and suggested that the desired fluid dynamics were recreated in the fabricated device.

Next, the unidirectionality of perfusion of the demonstration UniChip was tested. Red dye placed in one reservoir flowed to the other reservoir through the top ($a_1$, $a_2$), center ($C_u$) and bottom ($b_1$) channels (FIG. 7B). Once the device was flipped (FIG. 7C), blue dye replacing red dye in the other reservoir flowed back to the initial reservoir through the top ($a_1$, $a_2$), center ($C_u$) and bottom ($b_2$) channels. Unidirectional flow was thus achieved within the center channel as shown by the black arrows. To test the backflow proof mechanism of the UniChip design in cases where valves fail or delay to close, we placed excessive fluid (purple dye) in the top reservoir that completely covered the passive valve and delayed the liquid-air interface formation (FIG. 7D). Purple dye flows to the other reservoir through the top ($a_1$, $a_2$) and the bottom channels ($b_1$, $b_2$). It only started to flow through the center channel in the designed perfusion direction (black arrow) when the interface began to form. Yet during the whole time, no backwards flow was observed. Together these results suggest that the demonstration UniChip can provide unidirectional perfusion at desired flow rate and shear stress with an integrated mechanism preventing backwards perfusion.

3) HUVEC Responses on UniChip Versus BiChips

Next, the application of UniChip devices for long-term dynamic culture of shear stress-sensitive tissues was evaluated. Endothelial cells (ECs) were used for testing purposes. ECs lining the inner layers of the vasculature are directly exposed to hydrodynamic forces (e.g. shear stress induced by blood flow) that have been shown to modulate endothelial proliferation, function and inflammatory phenotype. Disturbed flow profiles often correlate with the localization of elevated inflammation and atherosclerotic lesions.

Figure 8:
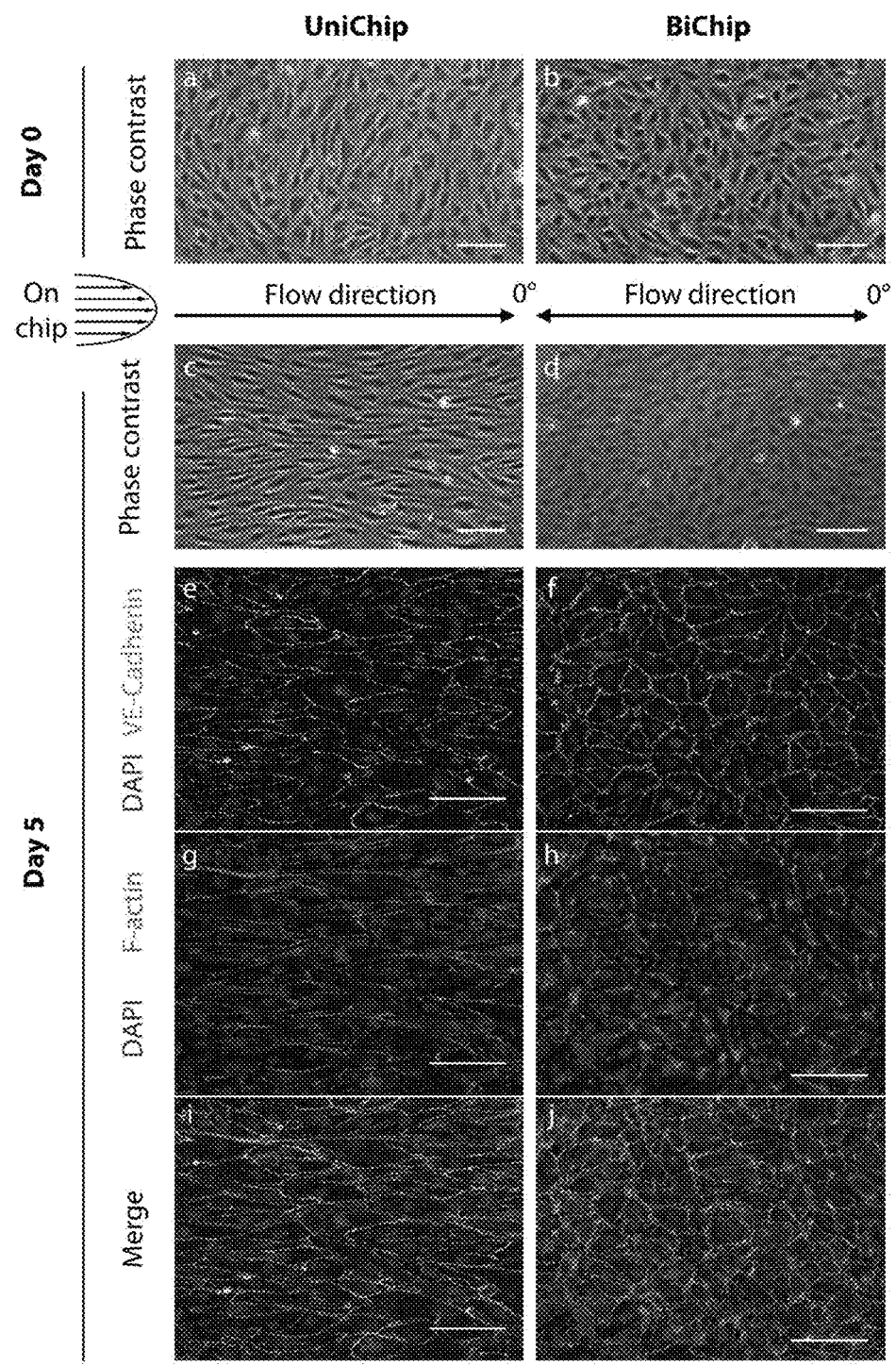
FIGS. 8A-J illustrate the UniChip and BiChip perfusion elicit differential responses in cell morphology and distribution of VE-cadherin and F-actin. Phase contrast images of HUVECs on UniChips and BiChips before and 5 days after flow onset show clear cell elongation and realignment to the flow direction in UniChip perfused cells (FIG. 8C vs.

HUVECs were seeded on the cell inserts of Unichip and BiChip devices at a same density and assembled all devices 24 hr later (day 0, FIGS. 8A-8B). To assess the impact of a longer duration of shear stress exposure rather than the transient response to the onset of flow, the cultures were maintained onchip for 5 days. The magnitude of shear stress acting on the ECs was estimated to be around 5.3 dyne/cm2. Visible remodelling of endothelial monolayers on the UniChip devices was observed by phase contrast microscopy by day 3. That became clearly significant by day 5 (FIG. 8C). Endothelial cells were elongated and aligned in the direction of flow, matching EC morphology under laminar flow. In contrast, endothelial cells exposed to bidirectional perfusion on the BiChips remained a polygonal shape as seen in traditional static culture, and showed no evident preference for orientation (FIG. 8D).

Next, the expression and distribution of VE-cadherin, an endothelial specific adhesion molecule at the cell-cell junctions that modulates endothelial permeability, was investigated. It is a major player in the mechanosensory complex and is considered responsible for cellular response to shear stress. Immunofluorescence staining revealed dense and continuous networks of VE-cadherin outlining the contours of ECs cultured on UniChip devices (FIG. 8E), while the distribution of VE-cadherin in ECs on BiChips was intermittent and diffusive (FIG. 8F). These results reflected cell junction remodeling and differential redistribution of VE-cadherin in response to different flow patterns. The results were consistent with in vivo observations of stronger pericellular staining of VE-cadherin at locations associated with pulsatile flow with net forward component than at places with complex and reciprocating flow. The results were also in line with in vitro studies that showed continuous versus intermittent staining of VE-cadherin under laminar versus reciprocating flows.

Figure 9:
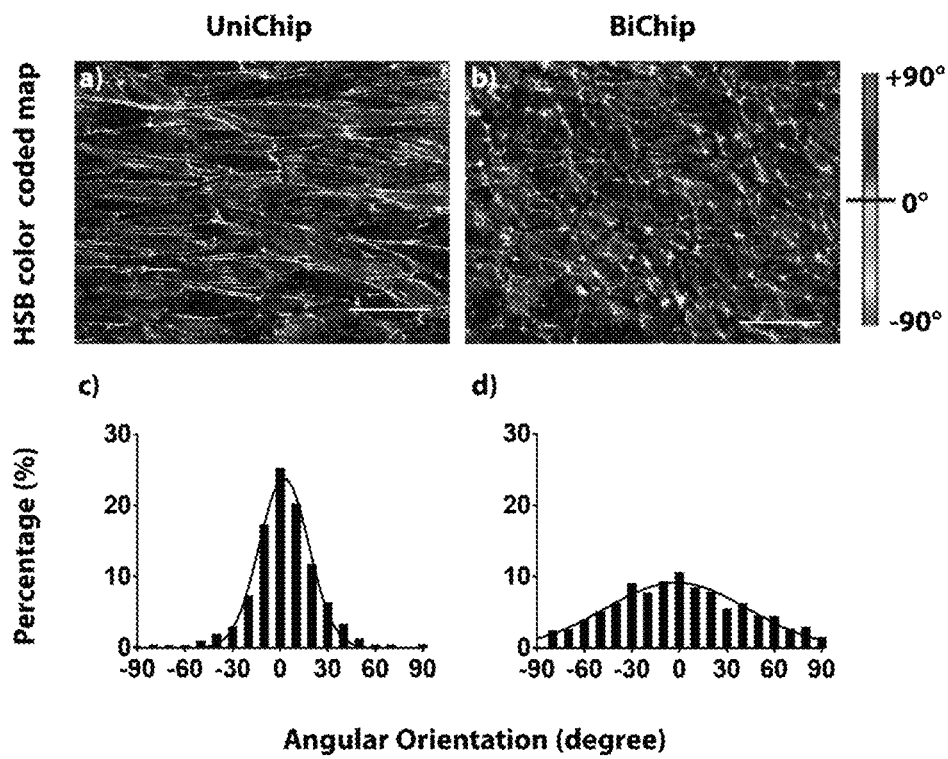
FIGS. 9A-D illustrate the visual and quantitative analysis of F-actin alignment in HUVECs cultured on UniChip and BiChip devices. The HSB (Hue: local orientation; Saturation: coherency; Brightness: from the original image) color coded maps derived from representative F-actin staining images reveal that a majority of F-actin in UniChip cultured cells aligned to the flow direction (FIG. 9A), while the spectrum of F-actin orientation in BiChip cultured cells is much broader (FIG. 9B). The quantitative graphs corresponding to FIGS. 9A and 9B are shown in FIGS. 9C and 9D, respectively.

Endothelial remodeling also involves reorganization of actin filaments (F-actin). F-actin organization was visualized using confocal microscopy with fluorophore conjugated phalloidin. Long and thick stress fibers were observed in the central areas of ECs cultured on UniChips and were oriented parallel to the flow direction (FIG. 8G, I), while short and thin filaments randomly orientated and presented mostly at cell periphery in cells cultured on BiChips (FIG. 8H, J). For further visual and quantitative analysis of F-actin alignment, an ImageJ directional analysis plugin was used—OrientationJ. The HSB (Hue: local orientation; Saturation: coherency; Brightness: from the original image) color coded maps of representative F-actin staining images confirmed F-actin alignment to the flow direction (0°, FIG. 9A) in UniChip perfused ECs, and more random orientation in BiChip cultured ECs (FIG. 9B). The dominant orientation of actin filaments in each cell was also analyzed with OrientationJ. The results for 2000 cells of each group were summarized in FIGS. 9C-9D. The distribution of endothelial F-actin orientation for the UniChip group fit a Gaussian curve with a mean around 0° and a standard deviation of 15.6°. A quarter of the EC population were oriented within ±5° of the flow direction, 63% within ±15°, and 82% within ±25°. For the BiChip group, although the F-actin orientation looked random, the quantitative analysis showed that it also follows a Gaussian distribution with a mean around 0, but the distribution is much more spread out with a larger standard deviation of 44.9°. Only 10% of ECs were oriented within ±5° of the flow direction, 28% within ±15°, and 43% within ±25°. UniChip perfusion for 5 days led to a majority of HUVEC F-actin aligning to the flow direction, while such realignment was much subtler in the population under oscillatory perfusion on BiChips. The observed actin remodeling for cell alignment under UniChip or BiChip perfusion match under laminar or oscillating disturbed flow.

Figure 10:
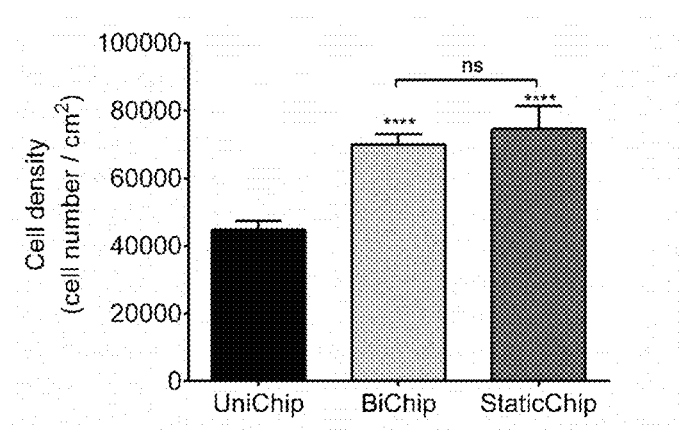
FIG. 10 illustrates endothelial cell density on UniChip, BiChip or in static culture.

In addition, although EC monolayers in all groups were confluent on day 5, the cell density differed among UniChip, BiChip or static dish cultured EC populations. There was no significant difference in the averaged cell densities from 10 representative views (567 μm×567 μm each) for the BiChip group (FIG. 10, 70004±1073 cells/cm$^2$) and the static control (74591±2368 cells/cm$^2$). However, the number for the UniChip group was about 40% lower (44728±1073/cm$^2$) compared to the other two groups. These results are not unexpected as laminar flow has been shown to restrict EC proliferation by suppressing cell transition from the G(1) to S phase of the cell cycle, while disturbed flow with reciprocating shear stress enhances EC proliferation and migration that often increase endothelial permeability.

In summary, the recirculating perfusion provided by UniChips elicited similar endothelial cell response as to laminar flows. Cell elongation and alignment to the direction of flow, continuous VE-cadherin network formation at the cell borders, actin stress fiber formation and realignment to flow, and lower cell density in UniChip cultured ECs were observed. These observations were in line with previously reported EC responses to laminar shear stress achieved with pumps or cone-and-plate devices, yet are distinct from the observations for BiChip cultured ECs or previously reported cell responses to oscillating disturbed flows.

Although preferred embodiments have been depicted and described in detail herein, it will be apparent to those skilled in the relevant art that various modifications, additions, subtractions, and the like can be made without departing from the spirit of the invention and these are therefore considered to be within the scope of the invention as defined in the claims that follow.

What is claimed:

1. A device comprising:
a reservoir base extending along a horizontal axis and having a first reservoir and a second reservoir positioned at opposing ends thereof and configured to hold a fluid, each of the first reservoir and the second reservoir having an inlet and an outlet extending through the reservoir base, the outlets of the first reservoir and the second reservoir located closer to the horizontal axis than the inlets of the first reservoir and the second reservoir, respectively, when the device is tilted between a forward tilted position, with respect to the horizontal axis, and a reverse tilted position, with respect to the horizontal axis; and
a channel layer comprising one or more inlet channels extending between and in fluid communication with the inlets of the first and second reservoirs, one or more outlet channels extending between and in fluid communication with the outlets of the first and second reservoirs, and a channel network comprising at least one channel extending between the one or more inlet channels and the one or more outlet channels; wherein the inlets, outlets, inlet channels, and outlet channels are positioned and configured such that:
when the device is tilted to the forward tilted position a first flow of the fluid from the first reservoir is directed from the outlet of the first reservoir, to the one or more outlet channels, through the channel network, and to the one or more inlet channels to both the inlet and outlet of the second reservoir, wherein the inlet of the first reservoir is configured to provide a passive valve such that fluid flow between the inlet of the first reservoir and the one or more inlet channels is prevented and the first flow of fluid traverses the channel network in a direction from the outlet channel to the inlet channel, and
when the device is tilted to the reverse tilted position i a second flow of the fluid from the second reservoir is directed from the outlet of the second reservoir, to the one or more outlet channels, through the channel network, and to the one or more inlet channels to both the inlet and outlet of the first reservoir, wherein the inlet of the second reservoir is configured to provide a passive valve such that fluid flow between the inlet of the second reservoir and the one or more inlet channels is prevented and the second flow of fluid traverses the channel network in the same direction from the outlet channel to the inlet channel.

2. The device of claim 1, wherein the first and second flows of fluid traverse the channel network in the same direction when the device is alternated between the forward tilted and the reverse tilted positions.

3. The device of claim 1, wherein the first and second flows of fluid provide a continuous flow of fluid across the channel network when the device is alternated between the forward tilted and reverse tilted positions.

4. The device of claim 1, wherein a physiological perfusion rate in an organ is simulated by the at least one channel providing a flow rate of the first and second flows of fluid to the channel.

5. The device of claim 1 further comprising:
a catalyst in the at least one channel of the channel network.

6. The device of claim 1, further comprising:
an insert having at least one chamber configured to house a catalyst and in fluid communication with the at least one channel of the channel network to deliver the first and second flows of fluid across the at least one chamber.

7. The device of claim 1, wherein the device is constructed of thermoplastics selected from the group consisting of polymethyl methacrylate (PMMA), polycarbonate, polystyrene, polyester, polyethylene, polyvinyl chloride, cyclic olefin copolymer, polypropylene, polyurethane, or polyetheretherketon (PEEK), silicone including polydimethylsiloxane (PDMS), glass, or metals.

8. The device of claim 1, wherein the first and second reservoir are coupled to the reservoir base by an adhesive, chemical bonding, or hot embossing.

9. The device of claim 1 further comprising:
a sealing gasket positioned between the reservoir base and the channel layer.

10. The device of claim 1, wherein the channel network comprises a plurality of channels.

* * * * *